United States Patent
Jones et al.

(10) Patent No.: US 10,909,990 B2
(45) Date of Patent: *Feb. 2, 2021

(54) METHODS AND SYSTEMS FOR SPEECH SIGNAL PROCESSING

(71) Applicant: Frontive, Inc., Beverly Hills, CA (US)

(72) Inventors: Charles Anthony Jones, Beverly Hills, CA (US); Kim Matthew Branson, Emerald Hills, CA (US)

(73) Assignee: Frontive, Inc., Beverly Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/655,814

(22) Filed: Oct. 17, 2019

(65) Prior Publication Data

US 2020/0051573 A1 Feb. 13, 2020

Related U.S. Application Data

(63) Continuation of application No. 16/279,418, filed on Feb. 19, 2019, now Pat. No. 10,460,734.
(Continued)

(51) Int. Cl.
| | |
|---|---|
| *G10L 15/22* | (2006.01) |
| *G10L 17/22* | (2013.01) |
| *G10L 21/18* | (2013.01) |
| *G10L 21/10* | (2013.01) |
| *G10L 17/26* | (2013.01) |
| *G16H 15/00* | (2018.01) |
| *G10L 17/00* | (2013.01) |
| *G10L 15/26* | (2006.01) |

(52) U.S. Cl.
CPC .............. *G10L 17/22* (2013.01); *G10L 17/26* (2013.01); *G10L 21/10* (2013.01); *G10L 21/18* (2013.01); *G16H 15/00* (2018.01); *G10L 15/26* (2013.01); *G10L 17/00* (2013.01)

(58) Field of Classification Search
USPC .................................... 704/275, 235, 9
See application file for complete search history.

(56) References Cited

U.S. PATENT DOCUMENTS

| | | | |
|---|---|---|---|
| 6,778,979 B2 | 8/2004 | Grefenstette et al. | |
| 7,181,438 B1 * | 2/2007 | Szabo ................. | G06F 21/6245 |

(Continued)

FOREIGN PATENT DOCUMENTS

| | | |
|---|---|---|
| JP | 2017 033581 A | 2/2017 |
| KR | 10-2014 0028975 A | 3/2014 |

(Continued)

OTHER PUBLICATIONS

PCT Search Report and Written Opinion regarding International Application No. PCT/US2019/018607, dated May 29, 2019, 9 pages.

*Primary Examiner* — Jakieda R Jackson
(74) *Attorney, Agent, or Firm* — Knobbe, Martens, Olson & Bear LLP

(57) ABSTRACT

Methods and systems for speech signal processing an interactive speech are described. Digitized audio data comprising a user query from a user is received over a network in association with a user identifier. A protocol associated with the user identifier is accessed. A personalized interaction model associated with the user identifier is accessed. A response is generated using the personalized interaction model and the protocol. The response is audibly reproduced by a voice assistance device.

30 Claims, 12 Drawing Sheets

Related U.S. Application Data

(60) Provisional application No. 62/693,164, filed on Jul. 2, 2018, provisional application No. 62/640,176, filed on Mar. 8, 2018.

(56) References Cited

U.S. PATENT DOCUMENTS

| | | |
|---|---|---|
| 2004/0143171 A1 | 7/2004 | Kalies |
| 2010/0063836 A1* | 3/2010 | Ballard .................. G16H 70/40 705/2 |
| 2011/0092779 A1 | 4/2011 | Chang et al. |
| 2012/0016678 A1 | 1/2012 | Gruber et al. |
| 2012/0035959 A1 | 2/2012 | Berdia |
| 2012/0036137 A1 | 2/2012 | Naidu |
| 2013/0132095 A1 | 5/2013 | Murthi |
| 2013/0325935 A1* | 12/2013 | Kiley .................. G06F 16/9535 709/203 |
| 2014/0081665 A1 | 3/2014 | Holmes |
| 2014/0088989 A1 | 3/2014 | Krishnapuram et al. |
| 2014/0113263 A1* | 4/2014 | Jarrell .................. G09B 23/28 434/262 |
| 2014/0163977 A1 | 6/2014 | Hoffmeister |
| 2014/0222436 A1 | 8/2014 | Binder et al. |
| 2014/0249817 A1 | 9/2014 | Hart |
| 2014/0278416 A1 | 9/2014 | Schuster |
| 2014/0278435 A1 | 9/2014 | Ganong, III |
| 2015/0162006 A1 | 6/2015 | Kummer |
| 2015/0199965 A1 | 7/2015 | Leak |
| 2015/0269342 A1 | 9/2015 | Swagger |
| 2015/0302002 A1 | 10/2015 | Mathias |
| 2015/0302857 A1 | 10/2015 | Yamada |
| 2016/0071517 A1 | 3/2016 | Beaver |
| 2016/0098393 A1 | 4/2016 | Hebert |
| 2016/0132290 A1 | 5/2016 | Raux |
| 2016/0165387 A1 | 6/2016 | Nhu |
| 2016/0378747 A1 | 12/2016 | Orr |
| 2017/0018007 A1 | 1/2017 | DeFrank |
| 2017/0076212 A1 | 3/2017 | Shams et al. |
| 2017/0161439 A1* | 6/2017 | Raduchel .......... G06F 16/24578 |
| 2017/0164319 A1 | 6/2017 | Skaaksrud et al. |
| 2017/0213545 A1 | 7/2017 | Kwon et al. |
| 2017/0359334 A1 | 12/2017 | Maddox et al. |
| 2018/0261216 A1 | 9/2018 | Leeb |
| 2019/0074077 A1 | 3/2019 | Kuo et al. |

FOREIGN PATENT DOCUMENTS

| | | |
|---|---|---|
| KR | 10-2016 0125543 A | 11/2016 |
| WO | WO 2017/210661 A1 | 12/2017 |
| WO | WO 2018/009397 A1 | 1/2018 |

* cited by examiner

512

602
UTILIZE USER IDENTIFIER TO
ACCESS USER MODEL AND
USER RECORDS

604
IDENTIFY TIME COMPONENT

606
MAP INTENT TO RESPONSE

608
POPULATE VARIABLES

610
GENERATE RESPONSE

METHODS AND SYSTEMS FOR SPEECH SIGNAL PROCESSING

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

COPYRIGHT NOTICE

A portion of the disclosure of this patent document contains material which is subject to copyright protection. The copyright owner has no objection to the facsimile reproduction by anyone of the patent document and/or the patent disclosure as it appears in the United States Patent and Trademark Office patent file and/or records, but otherwise reserves all copyrights whatsoever.

BACKGROUND OF THE INVENTION

Field of the Invention

The present disclosure generally relates to speech signal processing and more specifically to an interactive speech system.

Description of the Related Art

Conventional interactive speech systems fail to provide adequate personalization and fail to provide adequate interactivity with respect to user-specific medical care instructions.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

An aspect of the present disclosure relates to a system, comprising: a network interface; at least one processing device operable to: receive digitized audio data comprising a user query from a user; receive a user identifier associated with the digitized audio data; access a personalized interaction model corresponding to the user identifier; access a first protocol associated with the user identifier; utilize the personalized interaction model and the first protocol to generate a response; and cause the response to be audibly reproduced by a user device.

An aspect of the present disclosure relates to a system, comprising: a network interface; at least one processing device operable to: receive over a network using the network interface digitized audio data comprising a user query from a user, the digitized audio data streamed in real time from a user device; receive over the network using the network interface a user identifier associated with the digitized audio data; use a natural language processing engine to: translate the digitized audio data to text; identify, from the translated digitized audio data, a user intent associated with the query; identify, from the translated digitized audio data, a variable associated with the user intent; identify, using the user intent identified using the natural language processing engine, what computerized service to invoke; access from computer readable memory a personalized interaction model corresponding to the user identifier; access from computer readable memory a first protocol associated with the user identifier; access, using a computer resource, a current date and time; parse the first protocol to identify a first activity identified in the first protocol, the first activity identified in the first protocol associated with a specified date range and/or time period, that corresponds to the current date and/or time; utilize: the personalized interaction model, the first protocol, the identified first activity, the variable associated with the user intent, and the computerized service identified using the user intent, to generate a response to the user query; and cause the response to the user query to be transmitted to and audibly reproduced by the user device.

An aspect of the present disclosure relates to a computerized method, the method comprising: receiving over a network using a network interface digitized audio data comprising a user communication from a user, the digitized audio data received in real time from a user device; receiving over the network using the network interface data identifying the user; using a natural language processing engine to: translate the digitized audio data to text; identify a user intent associated with the communication; identify a variable associated with the user intent; identifying, using the user intent identified using the natural language processing engine, what computerized service to invoke; accessing a personalized interaction model corresponding to the data identifying the user; accessing from computer readable memory a first protocol associated with the user; parsing the first protocol to identify a first rule identified in the first protocol; utilizing: the personalized interaction model, the first protocol, the identified first activity, the variable associated with the user intent, and the computerized service identified using the user intent, to generate a response to the user communication; and causing the response to the user communication to be transmitted to and audibly reproduced by the user device.

BRIEF DESCRIPTION OF THE DRAWINGS

Embodiments will now be described with reference to the drawings summarized below. These drawings and the associated description are provided to illustrate example aspects of the disclosure, and not to limit the scope of the invention.

FIG. 6 illustrates an example response generation process.

DETAILED DESCRIPTION

Figure 1:
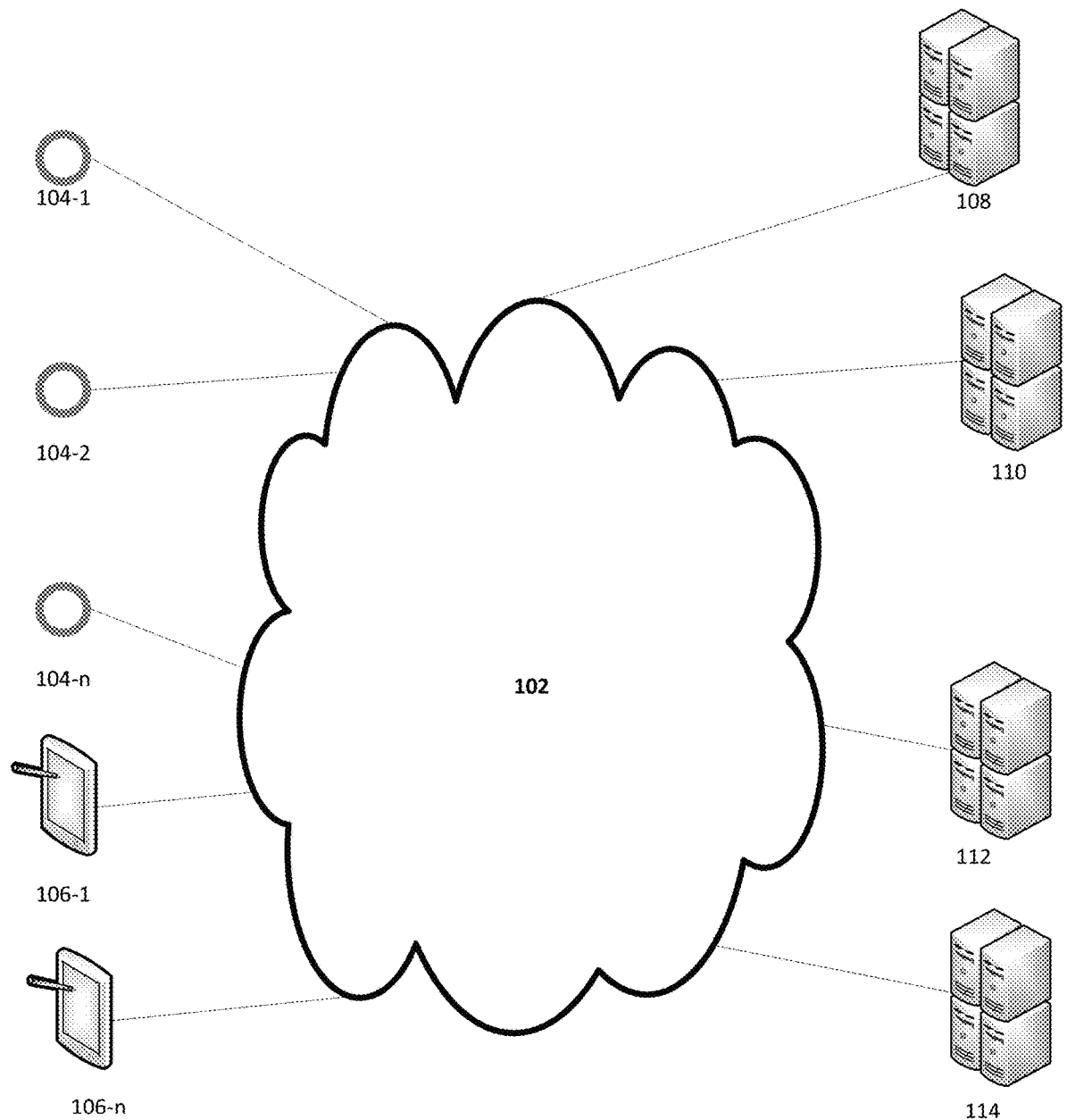
FIG. 1 illustrates an example multi-system architecture.

An aspect of the present disclosure relates to systems and methods for providing interactive voice-based and/or text-based sessions with personalized user responses, using contextual understanding. An aspect of the present disclosure relates to systems and methods that provide interactive voice-based and/or text-based sessions with a patient regarding patient care with individualized experiences. An aspect of the present disclosure relates to improving interactive voice-based and/or text-based sessions so that they are more natural, interpret user queries more accurately, and generate query responses with greater accuracy. An aspect of the present disclosure relates to systems and methods that access a static document, such as a patient care/protocol document, and utilize such document to provide interactive voice-based and/or text-based sessions with a patient regarding patient care. An aspect of the present disclosure relates to providing continuous speech recognition.

Although the following description generally discusses voice-based interactive systems, it is understood that a user may instead interact (using a user device) with the described systems via text, via images (a still image or a video comprising multiple images), or a combination of voice, text and/or images. For example, the user may submit queries via text, and the system may respond using voice (where the voice is reproduced by a user device comprising a speaker). By way of further example, the user may submit queries via voice (e.g., via a user device microphone), and the system may respond using text (which may be displayed by a user device display). By way of yet further example, the user may submit queries via text (e.g., using a user device keyboard), and the system may respond using text (which may be displayed by a user device display). Text-based interactions may be particularly advantageous where a user has hearing deficits, or where the user living situation (e.g., the presence of roommates) makes it difficult to have private interactive voice sessions.

By way of additional example, if a user submits a query (e.g., via voice or text) regarding a medication (e.g., "what medication am I supposed to take in the morning"), the interactive system may provide a digitized audible voice response (e.g., stating the medication name and how much medication the user is to take) to the user device for reproduction, and may access and transmit an image of the medication (e.g., a pill) for display on a user device display, optionally in associated with text providing instructions regarding the medication dosage. By way of still further example, if a user submits a query (e.g., via voice, text, and/or images (e.g., sign language queries)) regarding an exercise or medical operation, the interactive system may present provide an audible voice response (e.g., providing corresponding instructions), and may access and transmit a video to the user device (e.g., stream the video or download the video as a file to the user device) visually depicting how the exercise is to be performed or how the medical device is to be operated, and the user device may play the video on the user device display. For example, the video may include a recording of a person performing the exercise or an animation indicating how the exercise is to be performed.

Typically, when a new medical event (e.g., a new diagnosis, major surgery and/or an accident) occurs with respect to a patient, there is a significant increase in the complexity and/or volume of encounters with medical service providers, instructions and prescription drugs for the patient, which may last a significant amount of time.

For example, when a patient visits a doctor or undergoes a medical intervention (e.g., surgery, chemotherapy, dialysis, debridement, tests (e.g., colonoscopy), etc.), the patient may be provided with a document (sometimes referred to herein as a patient care document or protocol document) including preparation instructions prior to the intervention and/or instructions to be followed after the intervention.

By way of illustration, conventionally, when a patient receives a new diagnosis of a life-changing illness (cancer, major chronic condition) or undergoes surgery with a lengthy rehabilitation period, the patient typically receives a document including written instructions or protocols designed to: 1) answer common questions; 2) outline significant care management activities (e.g., preparation for a procedure, wound care, pain management, physical therapy, medications, etc.); and 3) set expectations regarding when certain activities should occur.

However, such conventional documents and instructions are both static and generic, requiring the patient and caregiver to interpret which details apply and which ones do not apply to their particular situation. Further, such documents and instructions are often confusing to patients, and yet patients may be embarrassed to ask the physician or other medical professional to explain the document, even when the patient may have many questions. For example, the patient (or caretaker or family member) may have questions regarding newly prescribed drugs, such as their purpose, side effects, interactions with other prescription drugs, non-prescription drugs, alcohol, recreational drugs, food, etc. By way of further example, the patient may have questions regarding protocols the patient is instructed to follow, such as what happens when, when are they allowed to perform certain activities (e.g., bathe, shower, perform certain types of exercise, etc.), and what happens next. The patient (or caretaker or family member) may also have questions regarding future encounters with medical service providers and events, such as when do they occur, what is the encounter (e.g., test or procedure) for, what can the patient expect, what should the patient do or not do in advance of the encounter and when, what happens if the patient misses an appointment, etc. Patients are often at home when such questions occur to them, but are reluctant to 'bother' the doctor after the visit. Likewise, doctors have little time during the office visit, may overlook what other doctors have prescribed, and often lack the knowledge to address all of these questions in the moment, leaving the patient rushed and confused. As a result, the chance of an avoidable adverse event increases significantly.

Still further, patients often lose such documents and are embarrassed to ask the physician for additional copies. Additionally, patients often lose track of how long it has been since they had a given procedure, and hence do not know the types and amounts of medications the patient should be taking at a given point in time. Yet further, some patients suffer from short term memory loss, so even if a patient is willing to call the physician regarding the care plan, the patient may forget the physician's clarifications and instructions. Still further, if a patient is willing to call the physician regarding the care plan, the patient may be inefficiently utilizing the physician communication system and may take the physician from other patients to answer routine questions.

To illustrate the potential complexity of a patient care plan, a relatively simple example will now be provided. The example care plan may be for a type of surgery.

Week 1
Medication
Take 2 (pain relief medication) pills every 4 hours.
Take 1 (antibiotic) pill after breakfast.
Take 1 (antibiotic) after supper.
Ice (body part).
Exercises Do 10 repetitions of (exercise #1)
Do 5 minutes of (exercise #2) twice a day
Follow-up Inspection
Visit doctor on Mar. 3, 2018 for inspection of incisions and removal of stitches.
Goals
Decrease pain
Range of motion <90 degrees (until stitches removed).
Weeks 2-3
Medication
Take 1 (pain relief medication) pills every 4 hours.
Ice (body part).
Exercises
Do 20 repetitions of (exercise #1)
Do 10 minutes of (exercise #2) twice a day
Goals
Decrease pain
Range of motion 120 degrees.
Weeks 4-6
Exercises
Do 20 repetitions of (exercise #1)
Do 20 minutes of (exercise #2) twice a day
Do 15 minutes of (exercise 3 2) twice a day
Goals
Range of motion 180 degrees.
Follow-up Inspection
Visit doctor on Apr. 3, 2018 for check-up.

In order to address one or more of the foregoing deficiencies, an aspect of the present disclosure relates to systems and methods to interactively interact with a patient (and/or other users, such as family members and caretakers). Patients are enabled to have clear question and answer interactions with the system with respect to the instructions (e.g., protocols) provided by their medical service providers. This makes the protocols more understandable and usable, which ultimately makes them easier for the patient to correctly follow.

For example, systems and methods are disclosed that are configured to respond to user questions regarding: instructions provided by a medical service provider (e.g., a physician, dentist, pharmacist, optometrist, therapist, nurse-practitioner, nurse, etc.); medications; medical conditions; lab and test results; and the user's medical history. Thus, aspects of the disclosure relate to providing a user-friendly system that enable patients to get answers to questions related to their medical condition and treatment (e.g., what, how, and why questions) and do so within the context of their specific medical history, personality, and individual preferences (which may be expressly provided and/or inferred based on patient behavior).

Although certain examples will be described with respect to interactions with a patient, the example processes and systems may similarly interact with family members and caretakers acting on behalf of the patient, and/or outside the context of medical care. Thus, for example, notifications described herein may be provided to a caregiver or family member so that the caregiver or family member may take an appropriate action, if needed, thereby reducing the incidence of avoidable adverse events.

An aspect of the disclosure relates to converting a health care/treatment document to interactive speech (and/or text) sessions, accessing patient data (e.g., demographics, name, medical conditions, etc.), verifying that the patient care instructions do not violate other patient care instructions and/or one or more protocols, receiving speech (and/or text) queries from the patient regarding the patient care document, and utilizing the document, patient data, and/or rules to provide a personalized verbal response to the patient. A natural language processing (NLP) engine may be utilized to accurately extract the entities (activities) and the time points within a given protocol document to transform the static instructions into computable files. The extracted entities and time points may be then transformed into an interactive, personalized, voice-enabled model (e.g., comprising program code stored in a file) utilizing a rules engine and a personalization engine, and optionally the current date and/or time (accessed from a local or remote clock device). The rules engine applies clinical rules (e.g., from evidence-based clinical decision support systems that are based on current standards of care). The personalization engine utilizes patient information (e.g., from the patient's clinical record, onboarding assessments, updated assessments, behaviors, and/or other patient data disclosed herein) to reduce the need for patient modification and interpretation of the patient's instructions. The personalized, voice-enabled model may provide more accurate, natural, and clear responses as compared to conventional voice interaction systems that use the same interaction model for large numbers of users.

For example, the personalized, customized interaction model may be generated based on a patient's profile. The profile may be generated using patient responses to certain questions, family members' responses to certain questions, caretaker responses to certain questions, and/or medical service providers' (e.g., physicians') responses to certain questions. The responses may be provided during an onboarding process and/or thereafter. There may be multiple types of onboarding. For example, there may be a first type of onboarding for a patient, and a second type of onboarding for someone involved in the patient's care. The responses may be utilized to assess the patient's level of engagement, preferences, motivations and beliefs.

By way of illustrative example, the patient may be asked to answer one or more questions whose answers may indicate how much information the patient wants regarding the patient's medical treatment, the degree to which the patient feels accountable for his/her own care, how much the patient relies on others for guidance in following instructions in a patient care document, how often the patient wants the system to ask certain questions, etc. The patient profile may also be based on logs indicating how often the patient utilizes the system, how many questions the patient asks per session and/or per time period (e.g., how many questions the patient asks per day, per week, per month, and/or other time period), what times of day the patient typically asks questions, how often the patient asks the same or similar question, how often the patient asks follow up questions after receiving an answer to a question, how long the interactive speech sessions typically last, how often or quickly the patient interrupts the response before it's completed. The patient profile may also be based on the patient's interests, hobbies, level of education, language comprehension, and/or personality (e.g., formal or informal, jokey or serious, etc.).

The patient profile may also be based on clinical information (e.g., electronic patient medical health records, patient-reported symptoms, medical providers' notes, demographics (e.g., age, gender, race), other information that may be relevant in determining potential drug side effects, normal/typical lab values, etc.).

Based on the patient profile, the customized interaction model may be configured to provide certain level of detail in responses to patient queries, use a certain level of vocabulary (e.g., 4th grade level, 8th grade level, high school level, college level, etc.) in responses to patient queries, use a certain level of formality in responses to patient queries (e.g., calling the patient by a nickname, or "Mr. Smith", "Ms. Jones," etc.), and/or provide certain types and/or amounts of ancillary content (e.g., jokes, aphorisms, interesting facts, historical information on drugs or medical procedures the patient has or will undergo, etc.) of interest to the patient, by way of example. Thus, utilization of the customized interaction model avoids the flood of irrelevant data that is typically generated and provided through a conventional online search or via interaction with a conventional chatbot.

In addition, an aspect of this disclosure relates to a machine learning engine that utilizes machine learning to generate an adaptive, multi-dimensional profile of a given patient to further enhance the relevance, accuracy, naturalness, and clarity of responses. Optionally a learning engine is utilized to build, revise, or augment a patient profile based in part on a patient's behavior during interactive speech sessions. For example, the learning engine may be configured to modify responses to a patient's queries based at least in part on the behavior of the patient with respect to previous responses.

By way of illustration, the system may respond to an initial patient question regarding what medication the patient should be currently taking. The system may provide a verbal response including the types, quantities, and times of day the patient should be taking medication, and may provide additional information such as what each medication is specifically intended to treat, medication side effects, and the like. If the patient interrupts the system while such additional information is being provided and asks the system to stop (e.g., terminates the session), the system may infer that the patient only wants the specific query answered, without additional information. On the other hand, if the system provides a certain level of information, but the patient has follow-up queries asking for still additional information, the system may infer that the patient appreciates in-depth information. Such patient behaviors may be used in dynamically determining the amount of information to be provided to the patient for further queries.

The interaction model may optionally be updated in response to detecting a new diagnosis, a new prescription, a change in the patient's drug regimen, a new care plan, a newly scheduled surgery, a newly performed surgery, a newly scheduled test, and/or receipt of new lab or tests results to further enhance the accuracy and clarity of communications generated using the interaction model. The interaction model may optionally also be updated periodically (e.g., once a day, once a month, once every two months, once every sixth months, once a year, or other time period, where the time period may a fixed time period or may change). For example, the patient and/or other users (e.g., caregivers, family members, etc.) may optionally be asked the same questions (or a subset thereof) to identify changes from a known baseline, and when such changes are detected, the model may be accordingly updated. Optionally, certain simple generic questions (not specific to the patient's medical condition) may be asked on a daily or weekly basis, such as "how do you feel on scale of 1-10?". Optionally, in addition or instead, certain specific questions relative to the patient's medical treatment protocol may be asked on a daily or weekly basis based on an expected change in condition (e.g., "on a scale of 1-10, what is the range of motion of your lower leg?").

Optionally, the system may enable the patient (or other authorized user, such as a caretaker or family member) to instruct the system to keep track of an identified issue (e.g., "Keep track of how I am feeling each day," "Keep track of my level of engagement," "Keep track of what I care about," etc.). Where appropriate, the system may generate corresponding questions for the patient, and ask the questions at a period specified by the tracking instructions (e.g., "Keep track of how I am feeling each day," "Ask me about my arms range of motion once a week") or at intervals determined by the system (e.g., twice a day, daily, every other day, weekly, etc.). The intervals may be determined by the system based on the issue being tracked. For example, if the user asks that a range of arm motion be tracked, the system may set the interval to be weekly. If the user asks that patient nausea be tracked, the system may set the interval to be twice a day. A lookup table may be defined mapping intervals to medical issues.

Patent data may also be received from IoT (Internet of Things) devices, such as wearables or other sensors that measure and/or track heart rate, exercise, glucose levels, blood pressure, and/or the like.

Responses to queries and/or other patient data (e.g., including medical history data, such as procedures, tests, results, drugs, etc.) may be shared by the system with the patient, caretakers, family members, and/or medical service providers, as appropriate. Further, such patient data may be automatically populated into the patient's electronic health care records maintained by one or more doctors. For example, by sharing such thorough and accurate medical data with medical service providers, medical service providers are provided with better visibility into patients' status between visits. Further, sharing such data facilitates obtaining a second opinion from a new physician or onboarding a new physician without patients having to maintain their medical information themselves. Thus, an aspect of this disclosure relates to systems and methods for providing a medical service provider with a consolidated patient history (e.g., via an application or browser accessible website). The consolidated patient history may be transmitted or securely transmitted to a designated destination.

An aspect of this disclosure relates to analyzing patient data (e.g., treatment plans, drug prescriptions, over the counter medications, supplements, scheduled medical procedures, scheduled medical tests, patient symptoms/responses, recreational habits (e.g., drugs, alcohol), and/or other data), and accessing evidence-based clinical decision support data to detect potentially harmful interactions (e.g., that may have been missed by the patient's medical treatment service providers (e.g., physician, dentist, pharmacist, optometrist, therapist, nurse-practitioner, nurse, etc.)).

The severity of the potential adverse interaction may be determined. If more than one potential adverse interaction is identified, the relative severity of each may be utilized in assigning priorities to each potential adverse interaction. In response to detecting such potentially harmful interactions, an alert may be generated and provided to the patient, family member(s), and/or caregiver(s) in the form of a specific question to ask a specific medical treatment service provider for clarification or correction. The alert may be provided via a notification service on a user device (e.g., smart phone, smart speaker, tablet computer, other computer, etc.), via email, or SMS/MMS message, an application, and/or otherwise. The alert may describe the potential adverse interaction, indicate the potential severity of the potential adverse interaction, and may provide a list of potential adverse interactions in ranked order. Thus, the system may identify the exact issues, prioritize the issues at least in part by severity, and direct the user to the specific medical treatment service provider(s) who can/should address each issue.

An aspect of this disclosure relates to analyzing patient data (e.g., treatment plans, drug prescriptions, electronic calendar entries, over the counter medications, supplements, scheduled medical procedures, scheduled medical tests, patient symptoms/responses, recreational habits (e.g., drugs, alcohol), and/or other data), and identifying specific activities such as future appointments, notices to arrange future appointments, pre-op/pre-procedure instructions (e.g., no water 12 hours before procedure, or when to discontinue a blood-thinner prior to surgery). In response to such identification, a notification/reminder may be generated at various times leading up to the event (e.g., a week prior, a day prior, and the day of the event) to remind the patient (or other user). The reminders may be provided via a networked voice assistance device (e.g., a networked speaker) utilizing a text-to-speech system, as described elsewhere herein. The reminder may be provided via a notification service on other user devices (e.g., smart phone, tablet computer, other computer, etc.), via email, or SMS/MMS message, an application, and/or otherwise. The disclosed system may provide such reminders at the appropriate time in response to a user instruction, such as the examples provided below:

Tell me when to take my drugs
Tell me when to perform specific tasks
Tell me when to see my medical service providers
Tell me when to schedule a new appointment Thus, the system may set reminders for the patient to remind the patient to take specific drugs at specific times as needed. The reminders are optionally set as alarms in order to activate the user device (e.g., smart networked speaker) and/or associated speech-to-text system without the patient having to trigger the system with the "Awake" phrase or control.

An aspect of this disclosure relates to detecting when a prescription needs to be refilled and generating a corresponding notification. Optionally, retail pharmacy applications and/or other pharmacy data sources are accessed, and the system detects when each of the patient's prescriptions were filled, how many pills (or how much liquid or powder) were dispensed and when it needs to be refilled. When the system detects that the patient has less than a specified threshold amount remaining (e.g., a 1 week or less remaining supply), a notification may be generated asking the patient (or other user, such as a caregiver or family member) if the patient wants to refill the drug. The patient may instruct (e.g., via voice, text, clicking on a reorder control displayed by an app, and/or the like) the system to refill the drug (e.g., "Yes, reorder my _____ prescription") and the system will transmit a corresponding electronic refill instruction to the pharmacy system. The system may also detect, via information accessed from the pharmacy system at which the refill order was placed, when the drug is ready for pickup, the pharmacy address, and the hours of operation. Such notifications may be similarly provided for non-prescription drugs, supplements or other supplies that are used on a regular basis.

The foregoing notifications may be provided to the patient, caregiver, and/or family member via the smart network speaker or via a notification service on other user devices (e.g., smart phone, tablet computer, other computer, etc.), via email, or SMS/MMS message, an application, and/or otherwise. Alerts and/or other actions may be generated when the system detects (e.g., from internal data and/or from data accessed from a pharmacy system) that drugs/supplies have not been re-ordered, delivered, or picked up. Thus, when notifications are provided to a caregiver or family member, the caregiver or family member may take an appropriate action (e.g., re-order or pickup medication, visit or contact patient, etc.) if the patient has failed to do so.

Optionally, the system enables a user to add, via a voice or text command, a non-prescription drug or supply to the patient's medicine list. Optionally, the system will detect conflicts with other medications or procedure and generate a corresponding alert.

An aspect of this disclosure relates to sharing patient data with authorized family members and/or caretakers. As discussed elsewhere herein, patient data is captured, and such data may be conveniently organized and presented in a way that the caregiver can easily retrieve specific items of data and receive automatic alerts regarding actions that require attention. The system may prioritize the actions based on potential severity and optionally enables users (e.g., caregivers and family members) to set their own threshold levels with respect to severity levels (e.g., non-critical, moderately important, critical, a critical level on a scale of 1-10, etc.) and corresponding notifications to make sure they are not overwhelmed with minor alerts and actions, but can instead focus on alerts and actions that are sufficiently important. Further, this ensures that authorized caregivers and family members are proactively informed of actions that need to be taken to prevent avoidable adverse outcomes. In addition, caregivers and family are provided with accurate medical data and enhanced visibility into the day-to-day status of the patient (e.g., using data collection from doctors and status information provided by the patient in response to system queries).

Certain aspects will now be discussed with reference to the figures.

With reference to FIG. 1, optionally, the disclosed voice interaction system 108 may be integrated with and utilize a third party voice assistance terminal devices 104-1, 104-2 . . . 104-n (e.g., networked speakers that may include a display) and one or more third party speech-to-text systems 110, such as those offered by AMAZON, GOOGLE, APPLE, and MICROSOFT. Optionally, the speech-to-text system 110 may be operated by the same entity as the interaction system 108 and optionally the speech-to-text systems 110 may be integrated into the voice interaction system 108.

For example, the instant voice interaction system 108 may be a web service hosted on a cloud system comprising a plurality of servers. The cloud system may be associated with the provider of the third party device and/or speech-to-text system 110, or the cloud system may be independent of such provider. The voice interaction system 108 may communicate with the speech-to-text system 110 via an application programming interface. The patient's query is streamed from the device to the speech-to-text system 110. The speech-to-text system 110 utilizes mapping information to determine what intent the request corresponds to. The speech-to-text system 110 may structure the request and transmit the structured request to the interaction system 108. The voice interaction system 108 may also communicate with one or medical record systems 112 (e.g., to access electronic patient health records, including clinical information), and one/or more medical clinical decision support systems 114 (e.g., that provide protocols and evidence-based recommendations for patient treatment based on current standards of care).

As discussed elsewhere herein, interaction system 108 may be configured to answer various user questions regarding protocols, interactions, encounters, drugs, refills, etc. The interaction system 108 may also be configured to ask the patient medical status information (e.g., "How are you feeling?", "What is your range of arm motion?", "On a scale of 1-10, what is your pain level?", etc.). In addition, the interaction system 108 may be configured to generate alerts, set alarms, track prescriptions, and the like.

By way of illustration, the interaction system 108 may be configured to answer some or all of the following non-limiting example questions regarding interactions, protocols, and encounters:

What is the purpose of Drug A?
What are the side effects of Drug A?
What interactions does Drug A have with other prescription drugs I am taking?
What interactions does Drug A have with non-prescription drugs?
What interactions does Drug A have with alcohol?
What interactions does Drug A have with recreational drugs?
What recreational drugs am I prohibited from taking while taking Drug A?
When am I permitted to take a bath?
When am I permitted to take a shower?
When am I permitted to take exercise?
When am I permitted to take exercise?
What medicine should I be taking?
What exercise should I be performing?
When should I reorder medicine?
When am I supposed to see the doctor?
What is this test for?
What is this procedure for, and what can I expect?
How should I prepare for the procedure?
What happens if I miss my appointment?

Optionally, the voice interaction system 108 may also communicate with users (e.g., patients, family members, caretakers, medical service providers) via applications installed on respective user terminals 106-1 . . . 106-n (e.g., smart phones, tablet computers, laptop computers, desktop computers, wearables, networked televisions, etc.) and/or via webpages accessed via respective browsers. For example, the application may be utilized to communicate with the voice interaction system 108 via text or voice, to present alerts to the user, to set user-specified alert-thresholds, to order medical supplies, to access and present a log of patient voice and/or text communications with the voice interaction system 108, and/or to provide analysis information generated by the voice interaction system 108.

By way of illustration, the voice interaction system 108 may analyze the patient's interaction with the voice interaction system 108, and report information to the application indicating some or all of the following example information: what questions the patient has repeatedly asked more than a specified threshold number of times, the average or median number of questions the patient asks per session, the average or median number of follow-up questions (e.g., asking for more detailed information than provided in a previous response) the patient asks per session, the average or median number of questions the patient asks per specified time period, how often the patient accesses the voice interaction system 108 over a given time period, and/or the like.

By way of further example, the voice interaction system 108 optionally monitors queries from a patient and determines whether there are recurring patterns of queries and/or whether there have been no or few queries (which may indicate non-use or limited use of the system). Such queries may be timestamped with the time that the query was received. Similarly, the voice interaction system 108 may examine various time periods (e.g., every hour, 6 AM-9 AM, 9 AM-12 PM, 12 PM-3 PM, 3 PM-6 PM, 6 PM-9 PM, 9 PM-12 AM, etc.) and based on the number of queries (or lack thereof) may take one or more predefined or dynamically determined actions. For example, if a patient asks several times in the same morning what medicine the patient is supposed to take (even if the patient utilizes different language or phrases in asking the question), this may be indicative of the patient being generally confused and so may be used to trigger a follow-up by the physician and/or a caregiver to determine the mental and/or health status of the patient.

The speech-to-text system 110 may receive a voice communication from a user (e.g., patient, caregiver, family member, etc.), and use a natural language processing engine to translate the speech to text. The text may be analyzed to determine if the user is invoking a "skill" and/or the user's "intent" (e.g., what a user is trying to accomplish, which may correspond to a service the user is requesting).

A skill may be an application (or "app") configured to work with the voice assistance device and the speech-to-text system. The application may optionally be hosted on servers associated with the speech-to-text system operator. The skill may be enabled by a user so that the user can access the skill. For example, the skill may be enabled via an application or via a voice instruction provided by the user using the voice assistance device. The skill may provide services corresponding to the intents. Although the following discussion utilizes terminology associated with AMAZON's ALEXA device and service, the discussion similarly applies to other platforms, such as GOOGLE's HOME device and service (which refers to apps as "actions" rather than "skills", and refers to the web service that can fulfill an intent as "fulfillment"). The services associated with the such devices may utilize respective interaction models, which may optionally be distinct from the personalized interaction models discussed elsewhere herein.

For example, sample words and phrases may be defined to indicate corresponding intents. By way of illustration, a mapping of words and phrases to intents may be generated and used to determine the user's intent. A given intent may have one or more associated variables (sometimes referred to as slot values) which are passed to the intent, such as the name of a medicine a user is inquiring about. Thus, for example, a medicine variable may be associated with a list of medicines prescribed for a given patient. By way of further example, an exercise variable may be associated with a list of exercises prescribed for a given patient. By way of yet further example, a diagnoses variable may be associated with a list of diagnosis prescribed for a given patient. By way of still further example, a proscribed food variable may be associated with a list of foods proscribed for a given patient.

Optionally, the system may utilize third party built-in intents (with associated mappings to utterances) when utilizing a third party user terminal and speech-to-text system, such as the ALEXA platform provided by AMAZON. For example, certain intents may be commonly used by different skill providers, such as "Help", "Yes", "No", "Stop", "Repeat," "Pause", "Resume", etc. The use of such built-in intents enables users to engage with different skills from different providers using consistent language.

A user may need to state a wake phrase (e.g., hey you, gizmo, "Acme", "Alexa", "OK Google", "hey Siri", etc.) prior to submitting a request (e.g., a query or instruction), in order to inform the terminal 104 or speech-to-text system 110 that a request is being provided by the patient (or other user) to the system.

The wake phrase may include one or more triggers words or other expressions (e.g., clapping of hands or a whistle). Optionally, rather than utilizing a wake phrase, a physical or touchscreen control may be utilized. In addition, a user may need to state an invocation phrase (e.g., "Frontive") to invoke a skill (e.g., provided by the voice interaction system 108). Optionally, in certain implementations, a wake phrase is not needed, and the voice assistant device may "wake" itself (or be woken by the voice interaction system 108 or the speech-to-text system 110), and push information or queries. By not needing a wake word, the voice interaction system 108 may initiate voice communications to the patient (or other user). By way of example, the voice interaction system 108 may automatically direct the user to take a certain action (e.g., "it's time to take your amoxicillin now"), or provide a voice notification (e.g., "your Celebrex refill will be ready for pickup at 3 PM today"), without the user providing a wake phrase.

Thus, for example, if a patient wanted to ask if he is permitted to drink alcohol, the patient might state "Acme, ask Frontive, if I can drink wine." In the forgoing phrase, "Acme" is the wake phrase, "Frontive" is the invocation phrase for the Frontive skill (provided by the voice interaction system 108), "can drink" is the intent, and "wine" is the variable.

Thus, by way of further example, if there is an intent used with respect to identifying proscribed foods ("ProscribedFoods"), the following utterances may be mapped to the "ProscribedFoods" intent, and used to invoke the intent:

"When can I drink (food name)"
"Can I drink (food name)"
"Can I have a (food name)"
"Can I eat (food name)"
"Is it ok to eat (food name)

When a user request (which may be an instruction or query) is received via a third party NLP system, such as that provided by the speech-to-text system 110, the speech-to-text system 110 may assign a unique identifier to the service associated with the skill ("Frontive" in this example). The speech-to-text system 110 may include the unique identifier when passing a user request to a corresponding service. Upon receipt by the voice interaction system 108, the service may verify the unique identifier is that assigned to the service, and if not, the service may transmit an error message to the speech-to-text system 110 and/or not further process the user request. By declining to process requests that do not have the correct skill identifier, processing resources are conserved.

In addition, a unique user identifier that identifies the user making the requested may be appended to the request. The user identifier may be automatically generated when the user enables the skill ("Frontive" in this example). Optionally, a timestamp indicating when the request was made may be appended to the request. Optionally, a unique request identifier may be generated and appended to the request.

Thus, when a request is received by the speech-to-text system 110, it may identify the intent (from the intent to utterances mapping) and any variable values, and transmit the intent, the variable values, the unique skill identifier, the unique user identifier, and the timestamp to the service hosted by the voice interaction system 108. The service may verify that the request is intended for the service and use the unique user identifier to locate and access the appropriate personalized model, medical records, profile, and/or other information associated with the user. The service may then process the request and provide an appropriate response.

A given session with a user may include more than one request. A user may explicitly end a session by speaking a termination phrase (e.g., "bye {invocation phrase}", "terminate", "exit", "all done", and/or other phrases).

If a user states the skill invocation phrase ("Frontive" in this example) without an utterance that is mapped to an intent (e.g., "I have questions for Frontive"), the service may generate a response, stating that more information is needed from the user, or listing available intents (or a subset thereof, such as the 4 most common requests from users, or the 4 most common requests from the specific user currently making the request). For example, the voice interaction system 108 may respond with the following "Did you want to ask about when you should take your medications, when is your next doctor's appointment, when can you take a bath, or something else?".

If the skill needs more information to complete a request, the voice interaction system 108 may conduct an interactive conversation with the user. For example, if the user asks "when does Frontive say I can stop taking medicine", without specifying the medicine being referred to, and where the patient is taking more than one medication, the voice interaction system 108 conduct the following conversation with the user:

Voice interaction system 108: "Which medicine are you asking about"
User: azithromycin
Voice interaction system 108: "You can stop taking azithromycin in three days, on April 28"

Figure 2:
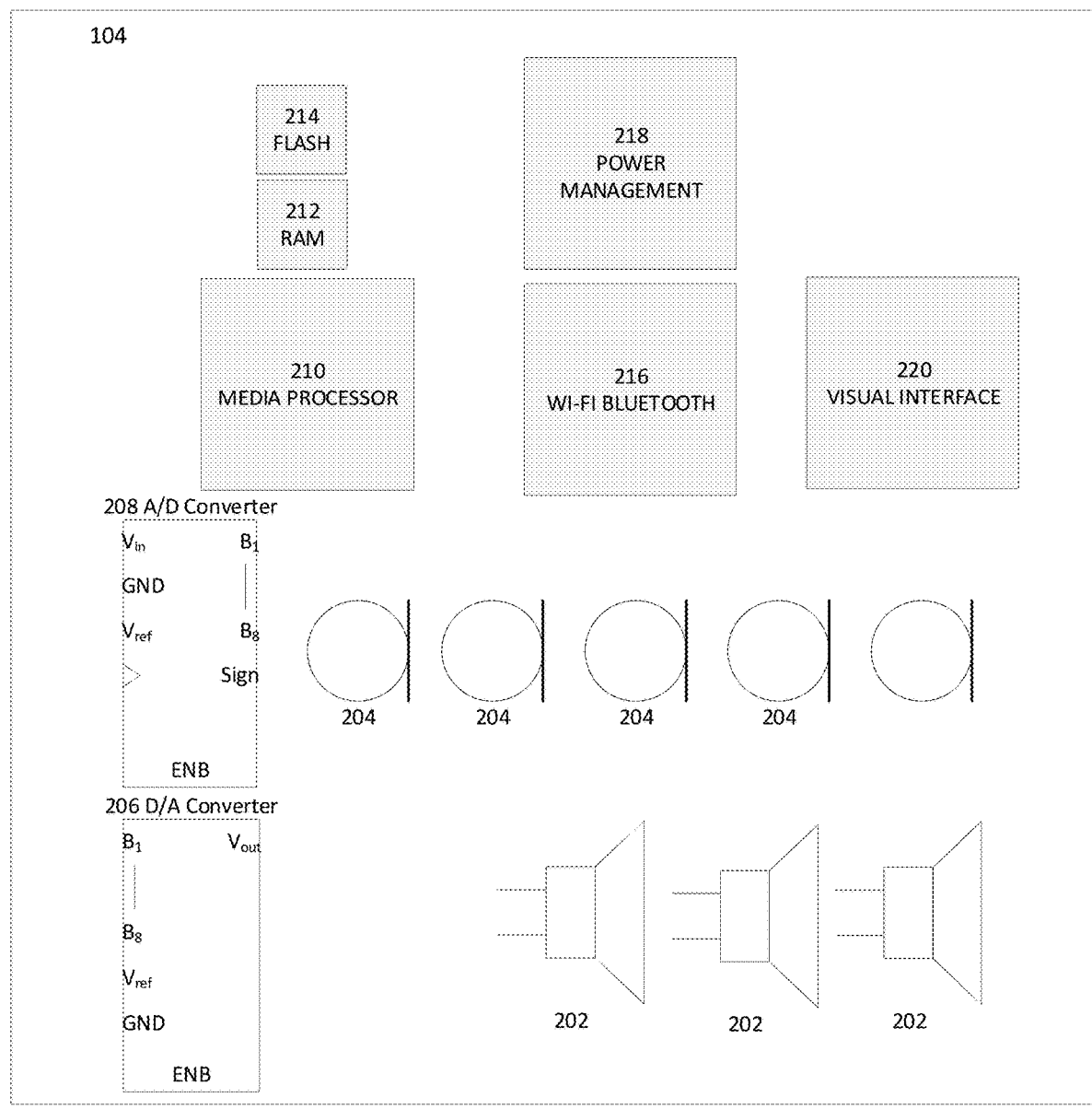
FIG. 2 illustrates an example voice assistant device architecture.

FIG. 2 illustrates certain components of an example voice assistant device 104. A device 104 may include one or more microphones 204, one or more speaker transducers 202 (e.g., cone speakers, electrostatic speakers, dome speakers, etc.), a digital media processor 210 (e.g., comprising a microprocessor, an audio processor, a visual interface/graphics processor, a memory controller, internal RAM, internal ROM), volatile memory 212 (e.g., SDRAM), non-volatile memory 214 (e.g., NAND Flash Memory), a wireless interface 216 (e.g., WiFi interface, a Bluetooth interface, a 4G cellular interface, a 5G cellular interface, etc.), a power management circuit 218, a digital-to-analog converter 206 (to convert digital information, such as digital voice data from the interactive system 108, to the analog domain to drive the speaker transducers), an analog-to-digital converter 208 (to convert analog information, such as voice signals from the microphones 204, to the digital domain for transmission to the interactive system 108)), a power supply (not shown), a visual user interface 220 (e.g., LED indicator lights, LCD display, OLED display, e-ink display, etc.), and/or the like. The speaker transducers 202 may include woofer speaker elements, midrange speaker elements, tweeter speaker elements, and/or other speaker elements.

Figure 3:
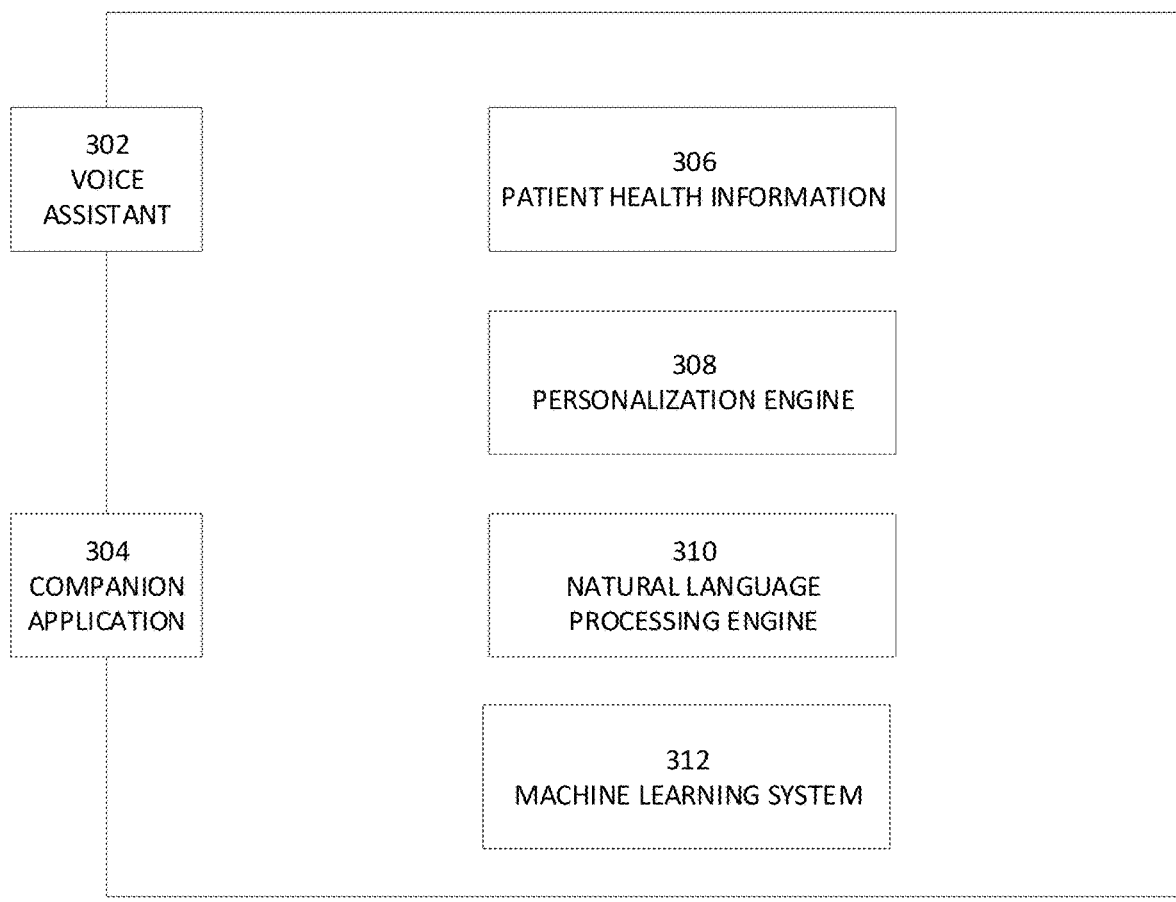
FIG. 3 illustrates an example voice interaction system.

FIG. 3 illustrates an example implementation of the voice interactive system 108. The example interactive system 108 includes a data store of patient profile information (e.g., health information accessed from electronic health records, information received via patient input, received from sensors (e.g., wearables or other devices) that measure user parameters (e.g., blood pressure, heart rate, glucose levels, etc.), received via caretaker input, via family member input, via medical service provider input, from pharmacies, etc.). In addition, the interactive system 108 includes a personalization engine used to generate an interactive model, as discussed elsewhere herein. A natural language processing engine 310 is provided which may perform optical character recognition (e.g., on patient care/protocol documents), syntax analysis (e.g., morphological segmentation, part-ofspeech tagging, parsing using a parse tree, sentence boundary disambiguation, word segmentation), semantics analysis (e.g., lexical semantics, named entity recognition, natural language understanding, relationship extraction, sentiment analysis, topic recognition and segmentation, stemming, word sense disambiguation, tokenizing, etc.), discourse analysis, co-reference resolution, automatic summarization, etc. The natural language processing engine 310 may also be utilized to produce natural sounding responses to requests using natural language generation that converts data into a natural language representation (e.g., using content determination (e.g., to determine what content, and what level of detail, is to be included), document structuring (e.g., to organize information provided in a response to a user query in a way to clearly convey the information), aggregation (e.g., the aggregation of similar information or sentences to improve the naturalness and understandability of responses), lexical choice, referring expression generation (that identifies objects and/or regions), and realization (e.g., creation of the actual response in accordance with proper grammar, syntax rules, orthography, and morphology).

A machine learning system 312 may be provided that is utilized to improve the performance of the natural language processing engine 312 and to improve the performance of the personalization engine 308. The machine learning system 312 may include one or more machine deep learning engines. The machine learning system 312 may analyze user interactions and utilize such analysis to improve the performance of the natural language processing engine 312 and/or the personalization engine 308.

The interactive system 108 may include a voice assistant interface 302 (e.g., to communicate with smart speakers and/or other voice systems) and a companion application interface 304 to interface with applications (such as those described herein) on user devices.

Figure 4:
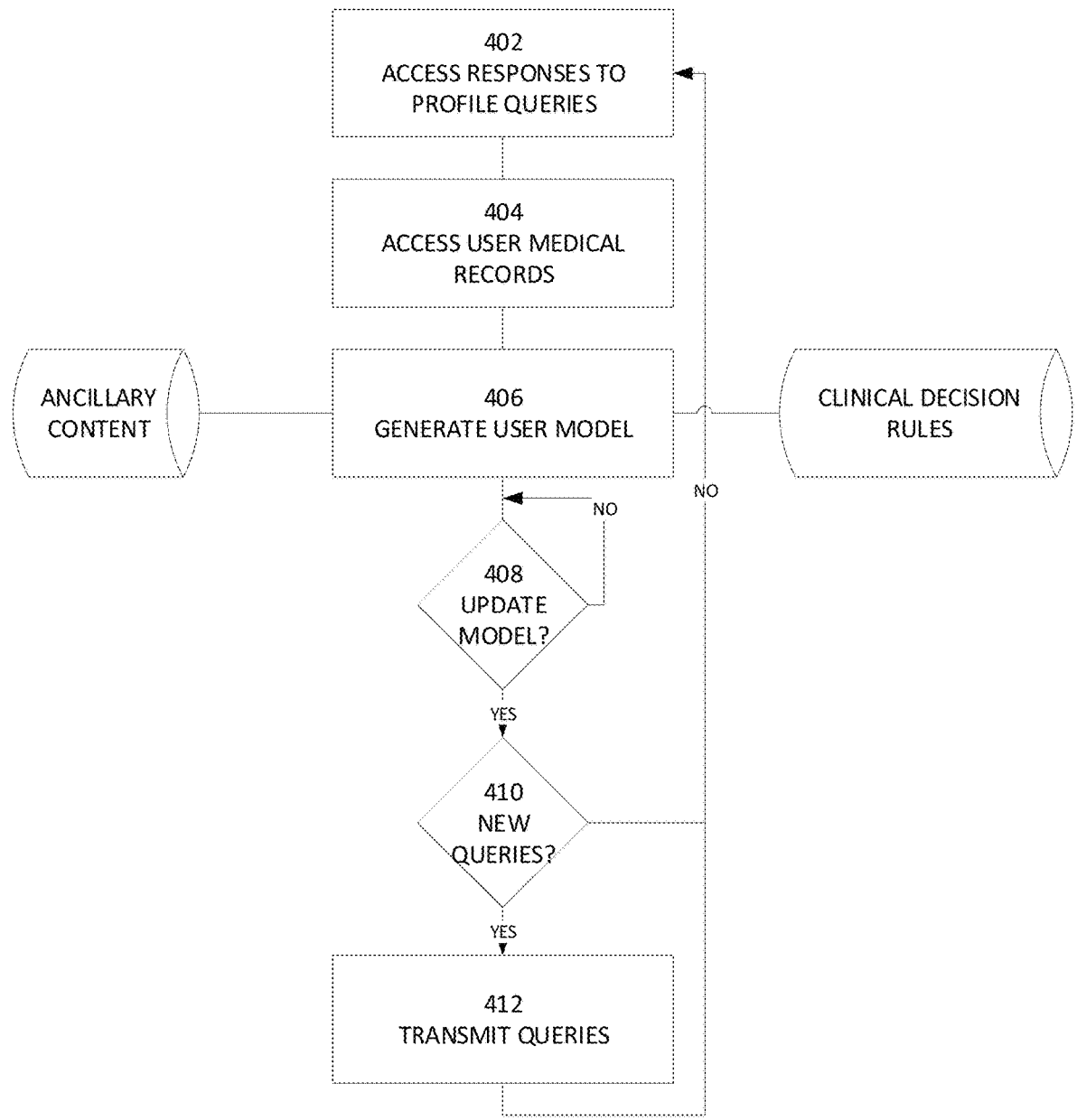
FIG. 4 illustrates an example personalized model generation process.

An example process for generating a personalized interaction model will now be described with reference to FIG. 4. As noted above, the personalized interaction model is configured to provide information in a manner suitable for the particular patient, and in a manner to make the patient more inclined to want to interact with the interaction system. Questions may be provided (e.g., via device 104, an application, a webpage, and/or otherwise) configured to extract information regarding the patient's personality (e.g., optimistic, pessimistic, upbeat, negative, etc.), the strength of the patient's motivation in self-care, one or more goals that are driving the patient (e.g., attending an upcoming event such as a reunion or family vacation), how much the patient relies on others for guidance in following instructions in a patient care document, the patient's desire for detailed information regarding medical matters, the sophistication of the patient's vocabulary (e.g., 4th grade level, 8th grade level, high school level, college level, other grade level, etc.), the patient's ability to comprehend medically-related information, the patient's ability to retain medically-related information, the patient's sense of humor (e.g., does the patient like jokes or clever repartee, or is the patient very serious), the subjects the patient is interested in (e.g., specified hobbies, sports, music, history, science, technology, art, literature, video games, movies, television, news, celebrities, religion, philosophy, medicine, geography, politics, cars, etc.), the patient's recreational habits (e.g., recreational drugs, alcohol), the patient's family situation (e.g., married, single, living alone, living with spouse, living with partner, how many children, how many children living at home, how many children living within a specified nearby geographical area, etc.), the patient's residence (e.g., house, apartment, one story residence, two story residence, stairs, etc.), demographics (e.g., age, gender, race, income, etc.), information from sensors (e.g., wearables, glucose sensors, or other devices) that measures user parameters (e.g., blood pressure, heart rate, oxygen levels, glucose levels, etc.), and/or other information. The foregoing information may include explicitly provided user preferences and information from which the patient's preferences may be inferred.

The questions may be provided to, and responses received (e.g., via a voice assistance device, an application installed on a user device, a website, etc.) from the patient and/or the patient's family members, caretakers, and/or medical service providers. The questions may be provided, and responses received, during an onboarding process (setup of an account for the patient) and/or thereafter. For example, the questions may be provided periodically (e.g., twice a year, once a year, once every two years, etc.) and/or in response to certain events (e.g., the occurrence of one or more of a selected set of medical interventions or encounters, a new health condition, a change in address, a user request that an update be performed, etc.), in order to ensure that the patient profile adequately reflects the patient's current situation.

At block 402, the patient's profile information is accessed. In addition to the responses to the profile queries, if the patient has already been utilizing the system, and the current model generation process is being executed to update the model, the patient profile may be also based on preference inferences made using logs indicating how often the patient utilizes the system, how many questions the patient asks per session and/or per time period (e.g., how many questions the patient asks per day, per week, per month, and/or other time period), what times of day the patient typically asks questions, how often the patient asks the same or similar question, how often the patient terminates a session while a response to a patient question is in the process of being streamed to the patient, how often the patient asks follow up questions after receiving an answer to a question, how long the interactive speech sessions typically last, information from sensors (e.g., wearables or other devices) that measure user parameters (e.g., blood pressure, heart rate, glucose levels, etc.), and/or the like.

At block 404, the patient's medical/health records are accessed from an electronic medical record system. The electronic medical/health records may include some or all of the following information: treatment plans (e.g., protocols), patient demographics, progress notes, vital signs, medical histories, diagnoses, medications, immunization dates, allergies, radiology images, lab and test results. Optionally, retail pharmacy applications and/or other pharmacy data sources are accessed, and the process detects when each of the patient's prescriptions were filled, how many pills (or how much liquid or powder) were dispensed and when it needs to be refilled.

At block 406, patient profile information and electronic medical/health record information are used to generate a customized, personalized interaction model for the patient. In addition, ancillary content that the patient may be interested may optionally be accessed and utilized in generating the personalized model. Optionally, information relevant to one or more protocols for the patient may be accessed from a clinical decision rules system and utilized to generating the model.

The personalization interaction model may define the verbal requests that the system will handle and the words that an end-user (e.g., a patient) may utilize in making such requests. The interaction model may also define what types of ancillary information (e.g., jokes, aphorisms, interesting facts, news, sports references, etc.) are to be presented to the user and when. The interaction model may also define what questions should be asked of the patient (and when) to determine if the model should be updated. The interaction model may also define what alerts and reminders should be provided to the patient (e.g., regarding taking medication, performing exercise, placing medication refills, preparing for a procedure, etc.). The interaction model may also define how the user should be referred to when speaking to the user (e.g., by first name, nickname, using a title (Dr., Ms., Mr., Mrs., etc.), or otherwise). Once generated, the model may be utilized.

At block 408, a determination is made as to whether the model should be updated. For example, as similarly discussed elsewhere herein, the process may detect (e.g., via the patient's medical records or interactions with the patient or other users) whether there has been a new diagnosis, changes in the user's status as determined from sensor readings (e.g., from wearables or other devices as discussed elsewhere herein), a new prescription, a change in the patient's drug regimen, a new care plan, a newly scheduled surgery, a newly performed surgery, a newly scheduled test, and/or receipt of new lab or tests results. In response to such detection and corresponding update rules, the process may decide whether or not the model is to be updated. By way of further example, the process may detect whether a scheduled update date has been reached, and if so, the process may determine that the model is to be updated.

If a determination is made that the model is to be update, at block 410 a determination is made as to whether the patient and/or other users should be queried regarding the patient. For example, the patient and/or other users (e.g., caregivers, family members, etc.) may optionally be asked the same questions (or a subset thereof) as asked during an onboarding process or for a previous update to identify changes from a known baseline. In certain cases, a determination may be made that it is not necessary to update query responses. For example, if a model update is being performed because the patient is being switched from one antibiotic to another antibiotic, there may be no need to provide queries to the patient, and the model may be updated utilizing prior query responses and the new prescription. If a determination is made the queries are to be provided, than at block 412, the queries are provided to the designated recipients (e.g., the patient, caretaker, family member, medical service provider, etc.). The process proceeds back to block 402, and the new (and optionally older) responses are accessed, and the process repeats to generate an updated personalized user model.

Figure 5:
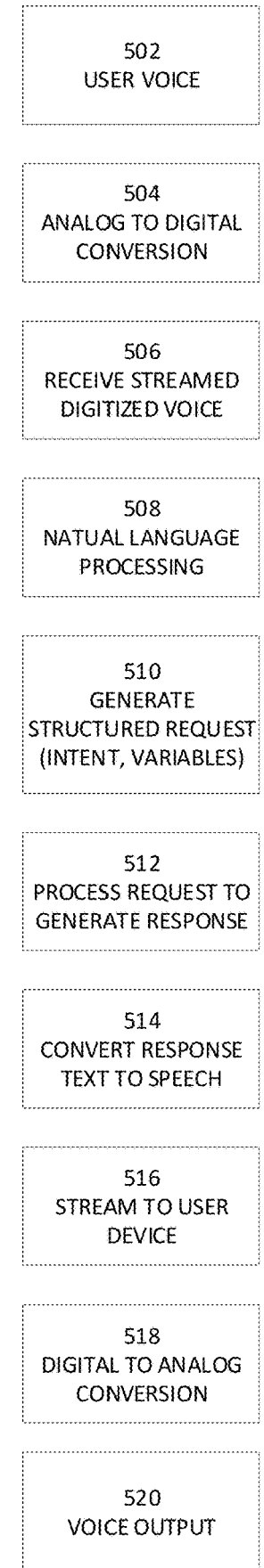
FIG. 5 illustrates an example voice session process.

FIG. 5 illustrates an example voice session process which may be performed utilizing systems and devices illustrated in FIG. 1. At block 502, the user makes a voice request. In real time, the user's voice is transduced by a microphone (e.g., of voice assistant device 104) and translated from the analog domain to the digital domain using an analog-to-digital converter. At block 506, the digitized voice may be streamed in real time from the voice assistant device to a speech-to-text system, which receives the digitized voice. At block 508, the speech-to-text system performs national language processing on the digitized voice, and identifies the skill being invoked, the intent, and any intent variable values. At block 510, the speech-to-text system generates a structured request indicating the intent and variable values. The system may transmit the structured request to a voice interactive system. The request may include a unique skill identifier, a unique user identifier, and a timestamp indicating when the request was made.

At block 512, the voice interactive system processes the user request and generates a personalized response utilizing a personalized interaction model (e.g., where the model is generated using processes discussed herein). At block 514, the process provides the response to a text-to-speech system, which converts the response into a format suitable for the voice assistant device. At block 516, the response is streamed to the voice assistance device. At block 518, the voice assistant device converts the received response to an analog signal using a digital-to-analog converter. At block 520, the voice assistant device utilizes the analog signal to drive one or more speakers, thereby providing a voice output. It is understood that several of the above operations may overlap with each other.

FIG. 6 illustrates an example response generation process, corresponding to block 512 in FIG. 5. At block 602, receives a structured request indicating the intent and variable values. The process analyzes the skill identifier to determine that the request is intended for the response generation process. If the skill identifier is correct, the process utilizes the unique user identifier to identify and retrieve the personalized interaction model for the user and to access health records for the user. The process identifies if there is a time component associated with the request. For example, certain requests, such as those that ask if the user can engage in certain activities in the next two weeks, the time element is specific. If, on the other hand, the request asks if the user can engage in certain activities (without specifying a time period), the process may infer that the request is related to the current time. By yet further example, certain requests may have no explicit or inferred time element. For example, if the request is regarding what a medication is used for, the response will be independent of any time period.

At block 606, the received intent is mapped to responses. For example, if the intent is regarding proscribed foods (e.g., the request is "What foods must I avoid"), the response may be "You cannot have" (list of proscribed foods). At block 608, any applicable variable values are used to populate corresponding response variables. For example, if the user asked "What medications should I take this morning", the response may be "This morning you should take the following medications: {medication.names}," where medication.names is a variable. The process may determine what medications the user is to take the current morning, and populate the response accordingly. At block 610, the final response is generated, which may include content not specific to the request and may include personalization content (e.g., "Good morning Liza! This morning you should take the following medications: one pill of Celebrex. Also, I know you like vegetables, so keep in mind that leafy greens like spinach and kale may help curb inflammation!").

Figure 7:
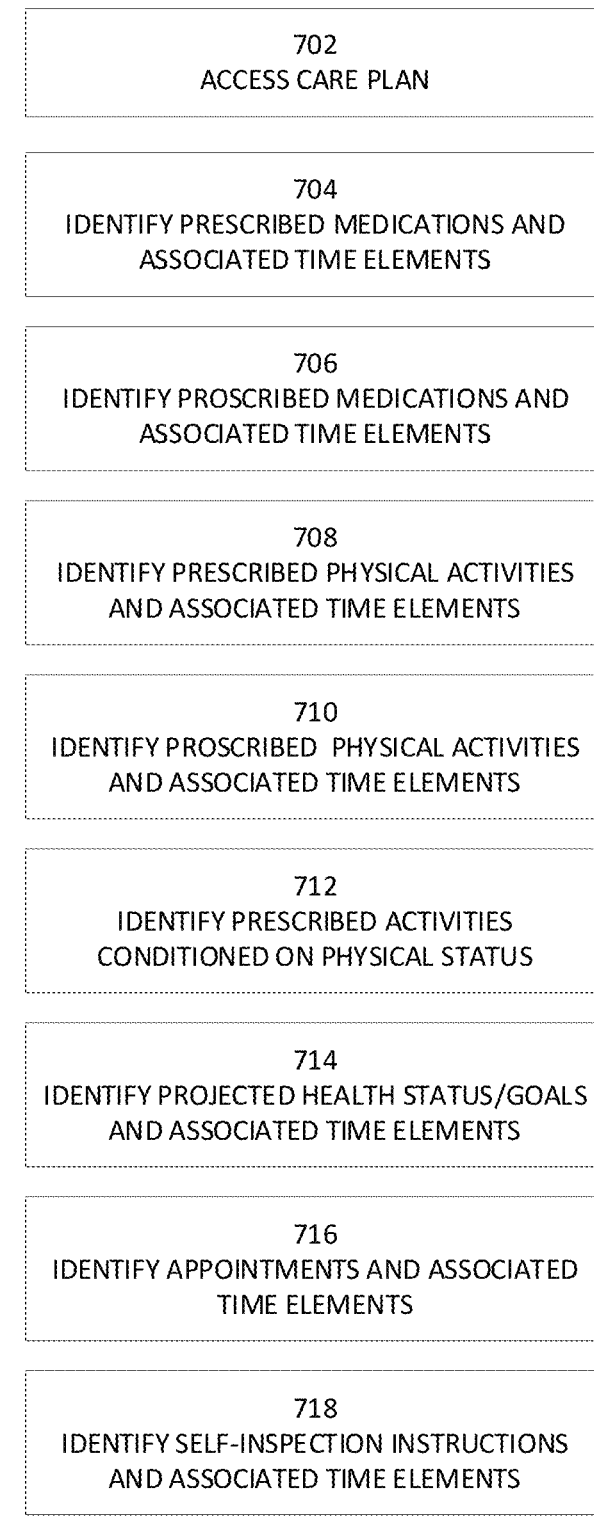
FIG. 7 illustrates an example natural language analysis of a protocol document.

FIG. 7 illustrates an example process for parsing a care plan, which may provide a protocol for treating a health issue, such as post-operational care. At block 702, a care plan is accessed. At block 704 the process utilizes natural language processing (NLP) to identify prescribed medications and associated time elements (e.g., what medications and the quantity of each medication the user is supposed to take each day or week). At block 706, the process utilizes NLP to identify proscribed medications and associated time elements (what periods of time the patient should not take the proscribed medications). At block 708, the process utilizes NLP identify prescribed physical activities and associated time elements (when the patient is to perform the prescribed physical activities). At block 710, the process utilizes NLP to identify proscribed physical activities and associated time elements (when the patient is not to perform the proscribed physical activities). At block 712, the process utilizes NLP to identify prescribed activities conditioned on physical status (e.g., where if the patient no longer feels pain, the user may be permitted to engage in certain physical activities). At block 714, the process utilizes NLP to identify projected health status/goals (e.g., degrees of movement, reduction in pain, increase in strength, etc.) and associated time elements. At block 716, the process utilizes NLP to identify appointments (e.g., with physicians, nurses, physical therapists, etc.) and associated time elements. At block 718, the process utilizes NLP to identify self-inspection instructions and associated time elements.

Figure 8:
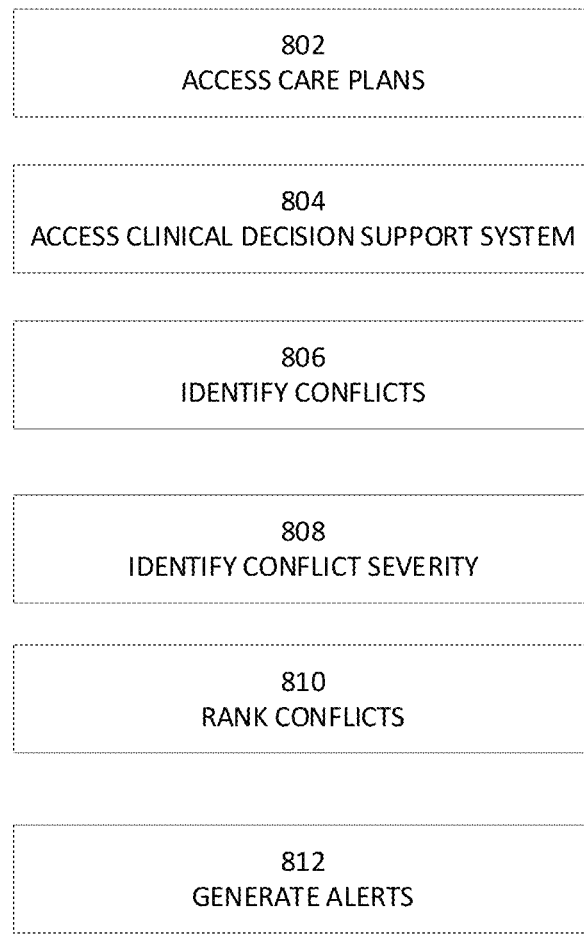
FIG. 8 illustrates an example conflict detection process.

FIG. 8 illustrates an example process for detecting care plan conflicts. At block 802, the process accesses one or more care documents from one or more medical service providers. At block 804, the process accesses one or more clinical decision support systems that provide rules and guidelines with respect to medical treatments and protocols. At block 806, the process utilizes the rules and guidelines from the clinical decision support systems to determine if there are any conflicts (e.g., adverse interactions) within a care document or between two or more care documents. Thus, for example, potential adverse drug-drug interactions, drug-lifestyle interactions, drug-procedure interactions, and unusual or alarming responses to drugs or a procedure may be identified.

For example, a first patient care document may indicate that the patient is to take a first medication and a second patient care document may indicate that the patient is to take a second medication, where the second medication in combination with the first medication will have an adverse effect on the patient (e.g., as determined from rules accessed from a clinical support system). By way of further example, a first patient care document may indicate that the patient is to eat a certain amount of a first food each day, while a second patient care document may indicate that the patient is to fast a day before a specified procedure.

Optionally, logically incompatible instructions may be identified in detecting a conflict (e.g., where one instruction indicates that the patient is to fast and another instruction says the patient is to eat three balanced meals; or where one instruction says to stay in bed and another instruction says to go on a 30 minute walk).

At block 808, the severity of the potential conflict may be determined. At block 810, if more than one potential conflict is identified, the relative severity of each may be utilized in assigning priorities to each potential conflict. At block 812, in response to detecting such potentially harmful interactions, an alert may be generated and provided to the patient, family member(s), and/or caregiver(s) in the form of a specific question to ask a specific medical treatment service provider for clarification or correction. The alert may be provided via a notification service on a user device (e.g., smart phone, smart networked speaker, tablet computer, other computer, etc.), via email, or SMS/MMS message, an application, and/or otherwise. The alert may indicate the potential severity of the potential conflict, and may provide a list of potential conflicts in ranked order. Thus, the process may identify the exact issues, prioritize the issues by severity, and direct the user to the specific medical treatment service provider(s) who can/should address each issue. Optionally, when a conflict is detected, the system may attempt to resolve the conflict.

Non-limiting examples of alerts are as follows:
Ask Dr. Acme about the interaction of Drug A with Drug B.
Ask Dr. Beta about the interaction of Drug A with upcoming medical procedure B interactions
Ask Dr. Gamma about your increase in heart rate when you take Drug A
Ask Dr. Delta about the interaction of Drug A with drinking alcohol to smoking marijuana As noted above, the system may optionally attempt to resolve the conflict using clinically-validated rules. For example, if the system determines that the user is to fast the day of a surgery, the system may optionally automatically determine, using clinically-validated rules, that the fasting takes precedence for at least the day of the surgery over any instructions regarding eating a well-balanced meal.

Figure 9:
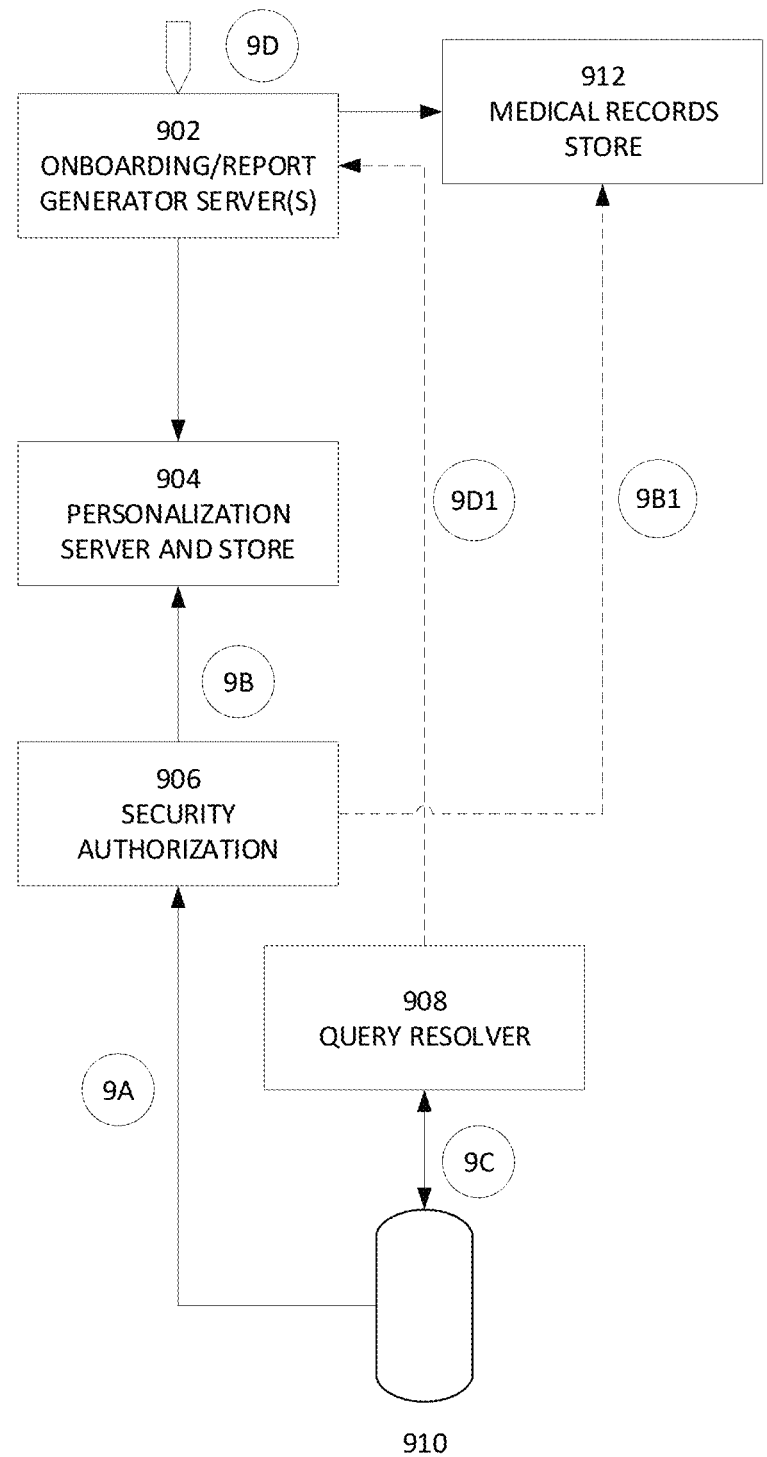
FIGS. 9-12 illustrate an example voice interaction system architecture and related processes.
Figure 10:
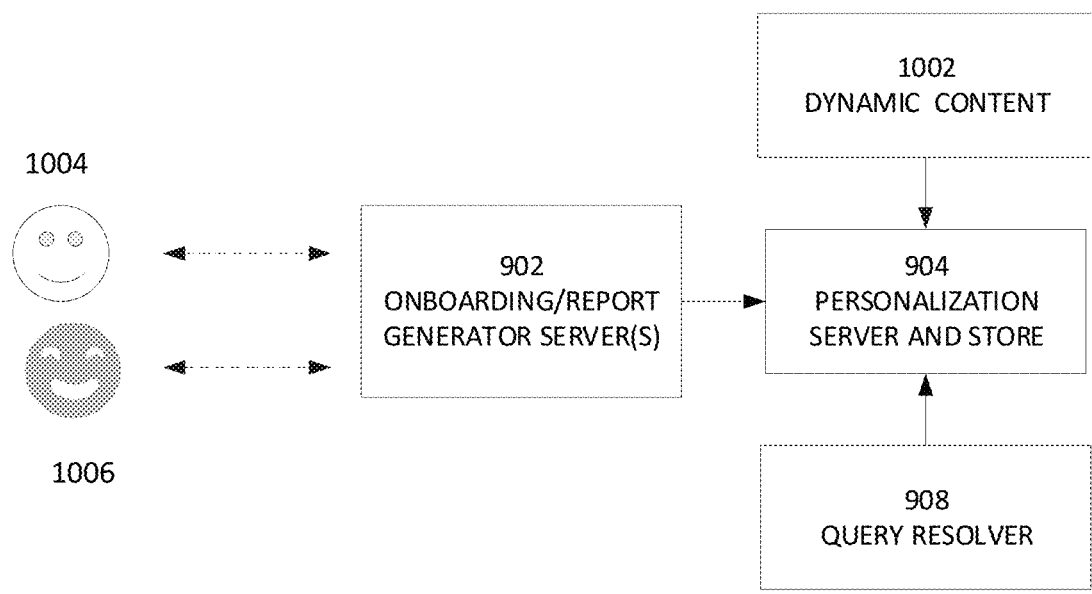
Figure 11:
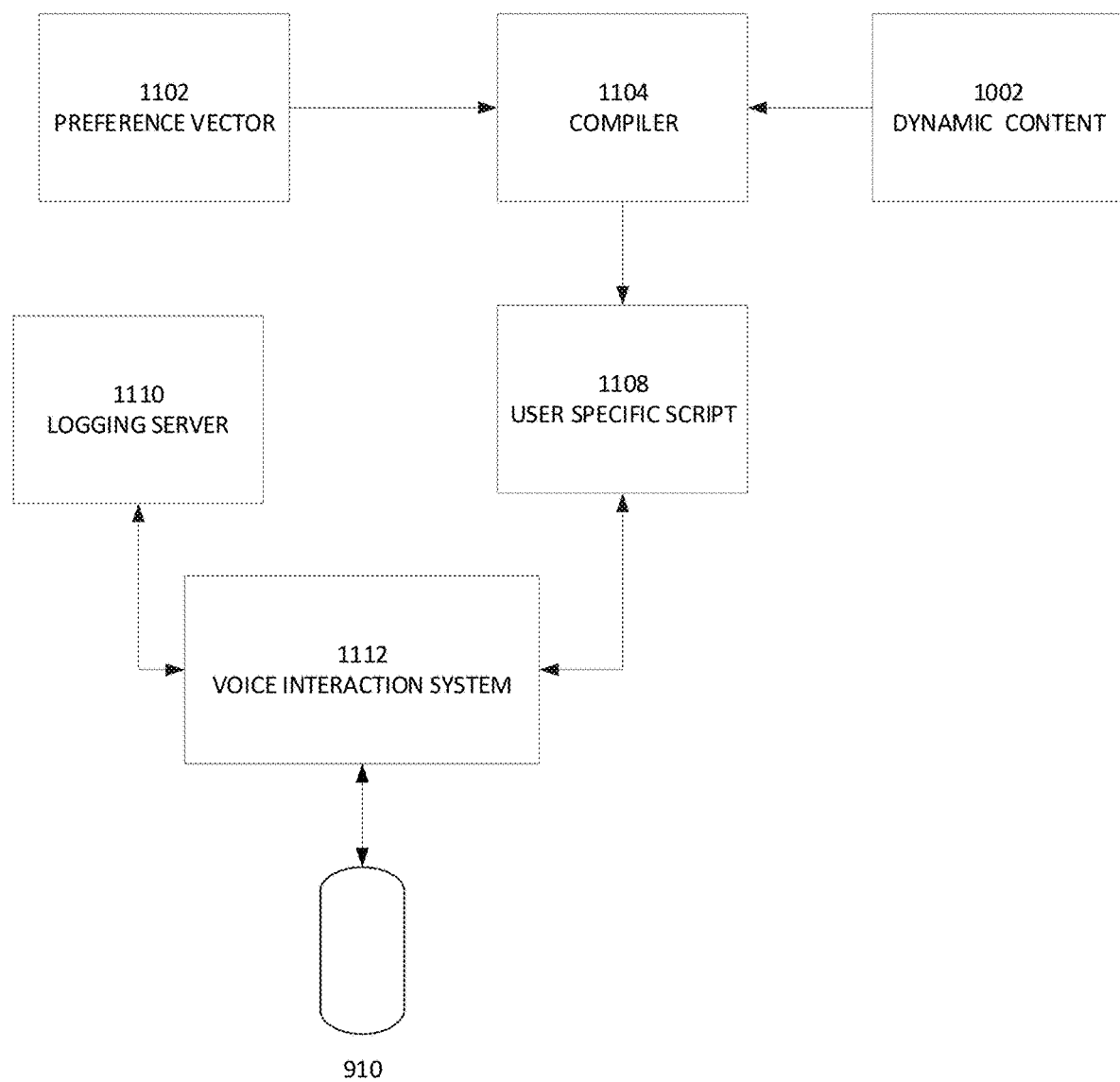

FIGS. 9-11 illustrate an example voice interaction system architecture and related processes. As illustrated in FIG. 9, the voice interaction system architecture may include an onboarding/report generator server 902 (although the onboarding module may be hosted on a different server than the report generator server), a personalization engine and data store 904, a security authorization module 906, a query resolver 908, and a medical records store 912. The onboarding server/report generator 902 may communicate with various user devices, such as a smart phone, tablet, smart television or other device, via a dedicated application and/or a browser. A voice assistant device 910, such as that described elsewhere herein (e.g., a smart speaker), may communicate with the voice interaction system.

At state 9A, a user is authenticated and a session is enabled by the security authorization module 906. For example, the authentication may be performed by the user speaking a code provided to or created by the user and comparing the spoken code with that associated with the user to determine if there is a match, and if there is a match, the user is authenticated and a session is enabled. By way of optional example, the code may be transmitted by the system to the user via email, SMS, or otherwise. The code may have been provided or generated during an initial onboarding process, such as that described elsewhere herein.

Optionally, in addition or instead, the authentication may be performed utilizing voice print analysis, wherein characteristics of a speaker's voice are used to identify the speaker or verify the speaker is who he is represented to be. For example, if a household has multiple members, speaker verification may be performed to verify the speaker is the registered user and not another family member. The user may undergo a voice enrollment procedure (e.g., during an onboarding process or at another time), where the user's voice is recorded and certain features (e.g., dominant tones) are extracted to form a voiceprint (e.g., a voice model) of the user. Optionally, the user may be provided with a written and/or oral script that the user is to orally rebate as part of the enrollment process.

The user voiceprint may be stored in association with the user's account and data. When the user later wants to interact with the system (e.g., using the voice assistant device 910), an authentication process may be performed. During authentication, a user voice input (e.g., word or phrase) may be compared with the previously created voiceprint. Optionally, the user is prompted via the voice assistant device 910 to repeat a phrase of one or more specified words (e.g., those the user spoke during the enrollment process) to provide the voice input to speed up the authentication process and make it more accurate. Optionally, the user may utilize speech of the user's own choosing in providing the voice input used in authentication to make the process easier for the user. If the features of the user's voice input match the voiceprint, then the user is authenticated. If the features of the user's voice input do not match the voiceprint, then the user is not authenticated and the user may be inhibited from accessing or utilizing personalization or medical data.

Optionally, a multistage authentication process may be performed. By way of example, a user may first need to provide an audible code (e.g., a verbal password), and then the system may ask the user (e.g., using the voice assistant device 910) certain security questions for which the answers were previously provided by the user (e.g., during an onboarding process) or for which answers are known from conversation interactions with the user. For example, the system may ask the user what street she grew up on, what her favorite sports team is, what is her primary doctor's name, etc. The user's answer may be compared against the known answer, and if they match, the user is authenticated and can access and/or utilize the personalization data (and if they do not match, the user is not authenticated and cannot access and/or utilize the personalization data).

Optionally, a first level of authentication may be provided in order for the user to interact with the system, where such interaction does not require access to the user's medical data but does utilize personalization vectors and data, and a second level where such interaction does require access to the user's medical data. For example, if the user is asking about the current news, is setting an alarm, or is asking a general question about a specific drug (e.g., "what are common side effects of acebutolol"?), then no knowledge of the user's medical condition or treatment is needed, and so a first level of authentication may be performed (e.g., using a first code, a voice print, etc.). If a response to the user's query (e.g., "What medications am I taking," "How many pills am I supposed to take", etc.), a second level of authentication may be performed (e.g., using a second code, a voice print, a security question, etc.). Thus, advantageously, more sensitive information (e.g., medical information) is optionally provided with heightened protection as compared with less sensitive information. Optionally, a security session timeout may be utilized, wherein if the user fails to provide a verbal input for a threshold period of time, the system may require the user be re-authenticated using one of the authentication techniques described herein. Optionally, the user may be able to specify the threshold period of time via a voice command or via the companion application.

At state 9B, the security authorization module 906 unlocks and enables the query resolver and the personalization engine. At state 9C, a digitized user query may be received via the voice assistant device 910. The user query may be provided to the query resolver 908. The query resolver 908 may request user data or vectors from the personalization store 904 and/or one or more medical record data stores 912. Publically available medical protocols may be accessed as well and are optionally treated as medical data with respect to certain questions (e.g., "what pills am I supposed to take this morning?"), because even though the protocol is public document, the fact that the user is following the protocol may not be public. A determination is optionally made as to whether a response to the query will necessitate access of the medical records store 912, and if so, a second level of authentication may be performed, as discussed above.

At state 9D, the onboarding/report generator server 902 interacts with a defined set of care providers (e.g., medical personnel, family members, etc.) and optionally the user. For example, the onboarding/report generator server 902 may generate alerts if it detects that the user has not utilized the system for a threshold period of time. By way of further example, if the user not placed a medication refill instruction or picked up a medication waiting for the user at a pharmacy (e.g., as determined by accessing information from a pharmacy computer system), a notification and/or a reminder may be generated. Optionally, the notifications and reports may be provided to the user in addition to or instead of to care providers. The system may optionally initiate a call between the user and one or more care providers (e.g., utilizing VoIP, where the user may optionally communicate via the voice assistant device 910) in response to a user request and/or in response to detecting certain specified events (e.g., the user has failed to place a refill order for a needed medication).

FIG. 10 illustrates an example personalization workflow. In this example, two types of users are interacting with the personalization workflow, a member (e.g., a patient), and one or more people in a patient care circle 1006 (e.g., a medical service provider, caretaker, family member, etc.). Optionally, each type of user undergoes an onboarding process via the onboarding server 902. The different types of users may undergo different onboarding processes, asked different questions, and different types information may be collected from different users.

By way of further example, the member/patient may be asked during an onboarding process or thereafter to answer questions whose answers may indicate how much information the member/patient wants regarding the user's medical treatment, the degree to which the member/patient feels accountable for his/her own care, how much the member/patient relies on others for guidance in following instructions in a user care document, how often the user member/patient accesses wants the system to ask certain questions, how the member/patient wants to be addressed (e.g., by which name/nick name), interests, hobbies, level of education, language comprehension, and/or personality (e.g., formal or informal, jokey or serious, etc.), etc.

Someone in the care circle may be, by way of example, asked questions about the member/patient (which may be regarding the same matters as asked of the member/patient) and/or questions regarding the types and frequency of information the person in the care circle would like to receive.

The information collected via the onboarding process may be utilized by the personalization server 904 to generate an initial preference vector. The preference vector may be utilized by the query resolver 908 as described herein and to determine what dynamic content 1002 should be provided to the member/patient 1004 or care circle user 1006.

FIG. 11 illustrates an example personalization workflow in greater detail. Referring to FIG. 11, a compiler 1104 receives a user preference vector 1102 and content 1106 (e.g., dynamic content/new content, such as the current day's news, daily jokes, facts, ribbing about the user's favorite sports team, etc.). The preference vector may be associated with a unique code corresponding to the user (member/patient or a care circle person). The preference vector may specify multiple templates for interacting with the user. The preference vector may be generated using expressly provided or inferred user preferences. For example, the preference vector may be generated utilizing information received from the member/patient and/or care circle persons during one or more onboarding processes, as similarly described elsewhere herein.

In addition, the preference vector may be updated based on the user's interactions with the system. For example, the interactions may include user queries, logs of the user's reactions to responses and other audible content (e.g., did the user ask a follow-up questions, did the user laugh at a joke told by the system, when queried as to whether the user liked an item of content (e.g., a joke, sports information, news, etc.) did the user answer yes or no, etc.).

As noted above, the user preference vector may also be based on logs indicating how often the user utilizes the system, how many questions the user asks per session and/or per time period (e.g., how many questions the user asks per day, per week, per month, and/or other time period), which part of a given workflow the user used and did not use, what times of day the user typically asks questions, what questions were asked, how often the user asks the same or similar question, how often the user asks follow up questions after receiving an answer to a question, how long the interactive speech sessions typically last, did the user ask for technical assistance, how often the user asked for a certain type of content (e.g., for another joke, for sports scores, stock prices, etc.), and/or how often or quickly the user interrupts the response before it's completed. The user's preference vector may also be based on the user's interests, hobbies, level of education, language comprehension, and/or personality (e.g., formal or informal, jokey or serious, etc.).

Optionally, the user preference vector may also be based on clinical information (e.g., electronic user medical health records, user-reported symptoms, medical providers' notes, etc.).

Using the preference vector 1102 and content 1106, the compiler 1104 optionally generates a user-specific program (e.g., a Python program)/script which will be generally referred to as a script) 1108. The program/script is deployed to other portions of the voice interaction system 1112 (e.g., query resolver). The user can then interact with the user-specific script using voice via the voice assistant device 910.

Figure 12:
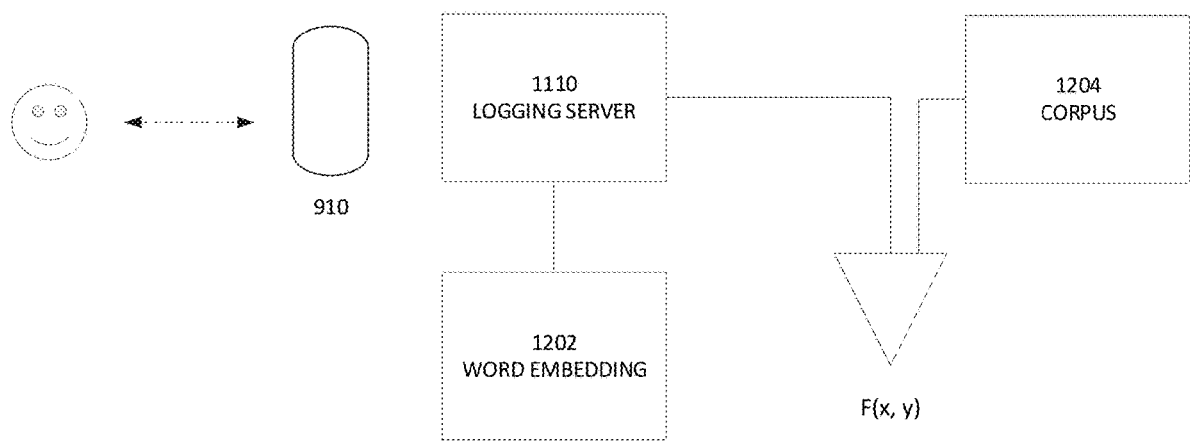

Referring to FIG. 12, an example user feedback loop is illustrated. As will be described the feedback loop utilizes voice inputs from a user to map user phrases to common formulas (e.g., f(x, y)), which may be utilized to determine intents, subjects, and verbs.

By way of illustration, a user may ask "what's the deal with [a medication name]?" via the device 910. However, the system may not know how to map the phrase to the desired intent. Such mapping failure may be logged by the logging server 1210. A word embedding module 1202 may be utilized to infer which words or whole phrases are intent synonyms. Word embedding may utilize a dense vector representation of phrases/words that try to capture the meaning of that phrase/word.

For example, words and/or whole phrases (including multiple words) may be expressed as vectors of co-occurring words and/or whole phrases. Optionally, in addition or instead, words and/or phrases may be expressed as vectors of linguistic contexts.

By way of further example, the vector may reflect the structure of the word/phrase in terms of morphology, word/phrase-context representation, global corpus statistics, and/or words/phrases hierarchy. The vector may be expressed as real numbers.

The mapping may be performed utilizing one or more techniques. For example, a phrase/word co-occurrence matrix, a neural network (such as a skip-gram neural network comprising an input layer, an output layer, and one or more hidden layers), or a probabilistic model may be utilized. Optionally, in addition to or instead of word/phrase embedding, distributional semantics models may be utilized that count co-occurrences among words by operating on co-occurrence matrices. Optionally, the mapping may be performed using a third party speech-to-text system, such as that described elsewhere herein. The third party speech-to-text system optionally only transmits an intent request to the voice interactive system if it is able to successfully match a user spoken phrase to one of a pre-configured set of intents. If the third party speech-to-text system fails to map the user phase to one of the pre-configured set of intents, optionally the third party speech-to-text system will not forward the user request to the voice interactive system. Optionally, the third party speech-to-text system will only transmit the intent request and any slot values captured as part of the user utterance, and not the full user utterance (whether or not successfully or unsuccessfully matched to an intent) to the voice interactive system.

By way of illustration, the process may examine words or phrases bounded by (on one or both sides) of a phrase/word at issue, and find other occurrence of other phrases/words with the bounding words/phrases (e.g., in a corpus to text 1204). The process may infer that words/phrases bounded by the same words/phrases have an equivalent meaning/intent. Optionally, stop word filtering may be performed where very common words (e.g., 'a', 'the', 'is', etc.) are excluded from consideration as bounding words.

By way of example, the phrases "what's the deal with [medication name]", "can you describe [medication name]", "tell me about [medication name]" may all be mapped to the same intent (e.g., the user wants information regarding [medication name]).

By way of illustration, words/phrases regarding medication may be mapped to a common function, such as f(x, drug name), that describes the medication.

In addition, the feedback loop process may include asking the user if the user liked certain content and/or query answers provided by the user, whether the user wants more or less information, whether the user wants to know about medication side effects, etc. Based on the user's responses, the user's preference profile and vector(s) may be updated. For example, if the user indicates that the user likes a first type of content and does not like a second type of content, the user's personalization vector(s) may be updated so that the user is provided more of the first type of content and less of a second type of content.

Thus, aspects of this disclosure relates to systems and methods that enable patients to be provided with access to useful information regarding their healthcare and clarify patient care instructions within their own home, without having to repeatedly contact their medical care service provider. Further, aspects of this disclosure relates to systems and methods that provide visibility and insight to patient behaviors and a patient's understanding of patient care documents to caregivers and physicians. Further, patient satisfaction is increased, patient healthcare is improved, while the workload on the physician and physician infrastructure is reduced.

The methods and processes described herein may have fewer or additional steps or states and the steps or states may be performed in a different order. Not all steps or states need to be reached. The methods and processes described herein may be embodied in, and fully or partially automated via, software code modules executed by one or more general purpose computers. The code modules may be stored in any type of computer-readable medium or other computer storage device. Some or all of the methods may alternatively be embodied in whole or in part in specialized computer hardware. The systems described herein may optionally include displays, user input devices (e.g., touchscreen, keyboard, mouse, voice recognition, etc.), network interfaces, etc.

The results of the disclosed methods may be stored in any type of computer data repository, such as relational databases and flat file systems that use volatile and/or non-volatile memory (e.g., magnetic disk storage, optical storage, EEPROM and/or solid state RAM).

The various illustrative logical blocks, modules, routines, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "may," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

While the phrase "click" may be used with respect to a user selecting a control, menu selection, or the like, other user inputs may be used, such as voice commands, text entry, gestures, etc. User inputs may, by way of example, be provided via an interface, such as via text fields, wherein a user enters text, and/or via a menu selection (e.g., a drop down menu, a list or other arrangement via which the user can check via a check box or otherwise make a selection or selections, a group of individually selectable icons, etc.). When the user provides an input or activates a control, a corresponding computing system may perform the corresponding operation. Some or all of the data, inputs and instructions provided by a user may optionally be stored in a system data store (e.g., a database), from which the system may access and retrieve such data, inputs, and instructions. The notifications/alerts and user interfaces described herein may be provided via a Web page, a dedicated or non-dedicated phone application, computer application, a short messaging service message (e.g., SMS, MMS, etc.), instant messaging, email, push notification, audibly, a pop-up interface, and/or otherwise.

The user terminals described herein may be in the form of a mobile communication device (e.g., a cell phone), laptop, tablet computer, interactive television, game console, media streaming device, head-wearable display, networked watch, etc. The user terminals may optionally include displays, user input devices (e.g., touchscreen, keyboard, mouse, voice recognition, etc.), network interfaces, etc.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A system configured to enable a user to obtain information related to a medical protocol using an audible query, comprising:
a network interface;
at least one processing device operable to:
generate a profile for a user using user data indicating:
how much information the user wants regarding medical treatments associated with the user, and
access a medical care record associated with the user, the medical care record comprising a first medical protocol including patient care instructions, the patient care instructions including:
a first patient care instruction associated with a first time period, and
a second patient care instruction associated with a second time period;
generate a first personalized interaction model using:
the user profile, and
the user medical care record comprising a first medical protocol including patient care instructions;
update the first personalized interaction model at least partly in response to a detection of a new medical care record or a modification of the first medical care record;
receive over a network using the network interface digitized audio data comprising a user query from a user, the digitized audio data streamed in real time from a user device;
receive over the network using the network interface an identifier associated with the digitized audio data;
utilize the identifier associated with the digitized audio data to access the first personalized interaction model generated using the user profile and the user medical care record;
use a natural language processing engine to:
translate the digitized audio data to text;
identify, from the translated digitized audio data, a user intent associated with the query, wherein identification of the user intent associated with the query comprises determining what computerized service the query corresponds to;
identify, from the translated digitized audio data, a variable associated with the user intent;
access from computer readable memory the first medical protocol;
access, using a computer resource, a current date and time;
identify one or more patient care instructions included in the first medical protocol associated with a specified date range and/or time period, that corresponds to the current date and/or time;
utilize:
the first personalized interaction model,
the first medical protocol,
the current date and/or time,
the identified one or more patient care instructions,
the variable associated with the user intent, and
the computerized service identified using the user intent, to generate a response to the user query; and
enable the response to the user query to be transmitted to and audibly reproduced by the user device.

2. The system as defined in claim 1, wherein the user device comprises:
at least a first microphone;
an analog-to-digital converter operatively coupled to the first microphone;
at least a first speaker transducer;
a digital-to-analog converter operatively coupled to the first speaker transducer;
a wireless interface;
a visual interface; and
a digital media processor operatively coupled to the analog-to-digital converter, the digital-to-analog converter, the wireless interface, and the visual interface.

3. The system as defined in claim 1, wherein the at least one processor is further operable to:
generate the user profile based at least in part on data provided by the user via an electronic form;
use the generated user profile to generate the first personalized interaction model;
monitor interactions of the user with the system;
use the monitored interactions of the user with the system to update the first personalized interaction model; and
interact with the user using the updated first personalized interaction model.

4. The system as defined in claim 1, wherein the at least one processor is further operable to:
detect a change in a status of the user, the change in status detected using a sensor; and
at least partly in response to detecting the change in the status of the user using the sensor, update the first personalized interaction model.

5. The system as defined in claim 1, wherein the computerized service is hosted by a third party system, the at least one processor is further operable to:
identify an identifier associated with the computerized service;
pass the computerized service identifier to the third party system;
pass at least a portion of the user query in association with the computerized service identifier to the third party system; and
receive data generated by the computerized service from the third party system,
wherein the generated response to the user query comprises the received data generated by the computerized service.

6. The system as defined in claim 1, wherein the at least one processor is further operable to:
perform natural language generation to thereby produce natural sounding responses to user queries, the natural language generation comprising converting data into a natural language representation using content determination, document structuring, aggregation, lexical choice, and/or referring expression generation.

7. The system as defined in claim 1, wherein the at least one processor is further operable to:
map phrases to intent utilizing a phrase/word co-occurrence matrix and/or a neural network comprising an input layer, an output layer, and one or more hidden layers.

8. The system as defined in claim 1, wherein the at least one processor is further operable to:
  identify a failure to map a user phrase to an intent; and
  log the failure to map the user phrase to an intent.

9. The system as defined in claim 1, wherein the at least one processor is further operable to:
  access a second medical protocol associated with the identifier associated with the digitized audio data;
  determine if the first medical protocol includes one or more instructions that conflict with one or more instructions in the second protocol; and
  at least partly in response to determining that the first medical protocol includes one or more instructions that conflict with one or more instructions in the second medical protocol, generate a corresponding personalized communication and cause the personalized communication to be transmitted to one or more destinations.

10. The system as defined in claim 1, wherein the at least one processor is further operable to:
  determine that an additional communication from the user is needed to generate a response to the user query;
  based on the determination that an additional communication from the user is needed to generate a response to the user query, generate a query requesting the additional user communication;
  cause the generated response to be audibly reproduced by the user device; and
  receive from the user device the additional communication from the user,
  wherein the response to the user query is generated using the communication from the user.

11. The system as defined in claim 1, wherein the variable is associated with a medicines prescribed for the user.

12. The system as defined in claim 1, wherein the at least one processor is further operable to:
  analyze a plurality of audio communications from the user;
  determine a frequency of communications from the user over a first time period; and
  based at least on the frequency of communications over the first time period, determine whether a communication is to be transmitted to a second user.

13. The system as defined in claim 1, wherein the at least one processor is further operable to:
  determine if a first event has occurred; and
  at least partly in response to a determination that the first event has occurred, generate an updated personalized interaction model.

14. The system as defined in claim 1, wherein the first personalized interaction model indicates how the user is to be addressed.

15. The system as defined in claim 1, wherein the first personalized interaction model indicates what type of ancillary content is be provided to the user in addition to the response to the user query.

16. The system as defined in claim 1, wherein the first one or more patient care instructions comprise a proscribed activity associated with a specified time period.

17. The system as defined in claim 1, wherein the at least one processor is further operable to authenticate the user by generating a voiceprint from the digitized audio data and comparing the generated voiceprint with a first voiceprint stored in memory, and authenticating the user at least partly in response to determining that the generated voice print corresponds to the first voiceprint.

18. The system as defined in claim 1, wherein the at least one processor is further operable to:
  select image content based at least in part on the identified first one or more patient care instructions;
  cause the image selected based at least in part on the identified one or more patient care instructions to be transmitted and displayed by the user device.

19. A computerized method, the method comprising:
  generating a profile for a user using user data indicating:
    how much medical information the user wants regarding medical issues associated with the user;
  accessing a medical care record associated with the user, the medical care record comprising a first medical protocol including patient care instructions, the patient care instructions including:
    a first patient care instruction associated with a first time period, and
  generating a first personalized interaction model using:
    the user profile, and
    the user medical care record comprising a first medical protocol including patient care instructions;
  receiving over a network using a network interface digitized audio data comprising a user communication from a user, the digitized audio data received in real time from a user device;
  receiving over the network using the network interface data identifying the user;
  utilizing the data identifying the user to access the first personalized interaction model generated using the user profile and the user medical care record;
  using a natural language processing engine to:
    translate the digitized audio data to text;
    identify a user intent associated with the user communication;
    identify a variable associated with the user intent;
  identifying, using the user intent identified using the natural language processing engine, what computerized service to invoke;
  accessing from computer readable memory the first medical protocol associated with the user;
  accessing, using a computer resource, a current date and time;
  parsing the first protocol to identify one or more patient care instructions included identified in the first medical protocol associated with a specified date range and/or time period, that corresponds to the current date and/or time;
  utilizing:
    the first personalized interaction model,
    the first medical protocol,
    the identified one or more patient care instructions,
    the variable associated with the user intent, and
    the computerized service identified using the user intent, to generate a response to the user communication; and
  causing the response to the user communication to be transmitted to and audibly reproduced by the user device.

20. The method as defined in claim 19, wherein the user device comprises:
  at least a first microphone;
  an analog-to-digital converter operatively coupled to the first microphone;
  at least a first speaker transducer;
  a digital-to-analog converter operatively coupled to the first speaker transducer;

a wireless interface;

a visual interface; and a digital media processor operatively coupled to the analog-to-digital converter, the digital-to-analog converter, the wireless interface, and the visual interface.

21. The method as defined in claim 19, the method further comprising:

generating the user profile based at least in part on data provided by the user via an electronic form;

using the generated user profile to generate the first personalized interaction model;

monitoring interactions of the user with the first personalized interaction model;

detecting a new medical care record or a modification of the first medical care record;

updating the first personalized interaction model using:

the monitored interactions of the user with the first personalized interaction model, and/or using the new medical care record or the modification of the first medical care record;

interacting with the user using the updated first personalized interaction model.

22. The method as defined in claim 19, the method further comprising:

detecting a change in a status of the user, the change in status detected using a sensor; and at least partly in response to detecting the change in the status of the user using the sensor, updating the first personalized interaction model.

23. The method as defined in claim 19, the method further comprising:

identifying an identifier associated with the computerized service;

passing the computerized service identifier to a third party system;

passing at least a portion of the user communication in association with the computerized service identifier; and receiving data from the third party system generated by the computerized service, wherein the generated response to the user communication comprises the received data generated by the computerized service.

24. The method as defined in claim 19, the method further comprising:

performing natural language generation to thereby produce natural sounding responses to user queries, the natural language generation comprising converting data into a natural language representation using content determination, document structuring, aggregation, lexical choice, and/or referring expression generation.

25. The method as defined in claim 19, the method further comprising:

mapping phrases to intent utilizing a phrase/word co-occurrence matrix and/or a neural network comprising an input layer, an output layer, and one or more hidden layers.

26. The method as defined in claim 19, the method further comprising:

accessing a second medical protocol associated with the data identifying the user;

determining if the first medical protocol includes one or more instructions that conflict with one or more instructions in the second medical protocol; and at least partly in response to determining that the first medical protocol includes one or more instructions that conflict with one or more instructions in the second medical protocol, generating a corresponding personalized communication and causing the personalized communication to be transmitted to one or more destinations.

27. The method as defined in claim 19, the method further comprising:

determining that an additional communication from the user is needed to generate a response to the user communication;

based on the determination that an additional communication from the user is needed to generate a response to the user communication, generating a communication requesting the additional user communication;

causing the generated response to be audibly reproduced by the user device; and receiving from the user device the additional communication from the user, wherein the response to the user communication is generated using the communication from the user.

28. The method as defined in claim 19, the method further comprising:

analyzing a plurality of audio communications from the user;

determining a frequency of communications from the user over a first time period; and based at least on the frequency of communications over the first time period, determine whether a communication is to be transmitted to a second user.

29. The method as defined in claim 19, wherein the first personalized interaction model indicates how the user is to be addressed.

30. The method as defined in claim 19, wherein the first personalized interaction model indicates what type of ancillary content is be provided to the user in addition to the response to the user communication.

* * * * *

UNITED STATES PATENT AND TRADEMARK OFFICE
CERTIFICATE OF CORRECTION

| | | |
|---|---|---|
| PATENT NO. | : 10,909,990 B2 | Page 1 of 1 |
| APPLICATION NO. | : 16/655814 | |
| DATED | : February 2, 2021 | |
| INVENTOR(S) | : Charles Anthony Jones | |

It is certified that error appears in the above-identified patent and that said Letters Patent is hereby corrected as shown below:

In the Drawings

In sheet 5 of 12, FIG. 5, reference numeral 508, Line 1, delete "NATUAL" and insert -- NATURAL --.

In the Specification

In Column 6, Line 65, delete "4th" and insert -- $4^{th}$ --.

In Column 6, Line 65, delete "8th" and insert -- $8^{th}$ --.

In Column 13, Line 35, delete ")" and insert -- ) " --.

In Column 14, Line 47, delete "108))," and insert -- 108), --.

In Column 15, Line 13, delete "included)," and insert -- included)), --.

In Column 15, Line 52, delete "4th" and insert -- $4^{th}$ --.

In Column 15, Line 52, delete "8th" and insert -- $8^{th}$ --.

In Column 23, Line 31, delete "script)" and insert -- script --.

In the Claims

In Column 29, Line 56, Claim 15, delete "is be" and insert -- is to be --.

In Column 32, Line 49, Claim 30, delete "is be" and insert -- is to be --.

Signed and Sealed this
Sixth Day of April, 2021

Drew Hirshfeld
*Performing the Functions and Duties of the
Under Secretary of Commerce for Intellectual Property and
Director of the United States Patent and Trademark Office*